United States Patent
An et al.

(10) Patent No.: US 10,874,860 B2
(45) Date of Patent: Dec. 29, 2020

(54) METHOD AND SYSTEM FOR DETERMINING A CARDIAC CYCLE PACE TIME IN ACCORDANCE WITH METABOLIC DEMAND IN A LEADLESS CARDIAC PACEMAKER SYSTEM

(71) Applicant: CARDIAC PACEMAKERS, INC., St. Paul, MN (US)

(72) Inventors: Qi An, Blaine, MN (US); Michael J. Kane, St. Paul, MN (US); Yinghong Yu, Shoreview, MN (US); Jeffrey E. Stahmann, Ramsey, MN (US); Pramodsingh Hirasingh Thakur, Woodbury, MN (US); Keith R. Maile, New Brighton, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 369 days.

(21) Appl. No.: 15/654,393

(22) Filed: Jul. 19, 2017

(65) Prior Publication Data

US 2018/0021582 A1 Jan. 25, 2018

Related U.S. Application Data

(60) Provisional application No. 62/364,599, filed on Jul. 20, 2016.

(51) Int. Cl.
*A61N 1/365* (2006.01)
*A61N 1/375* (2006.01)
(Continued)

(52) U.S. Cl.
CPC ......... *A61N 1/36585* (2013.01); *A61N 1/056* (2013.01); *A61N 1/36535* (2013.01);
(Continued)

(58) Field of Classification Search
None
See application file for complete search history.

(56) References Cited

U.S. PATENT DOCUMENTS 6,314,323 B1  11/2001  Ekwall
7,142,917 B2  11/2006  Fukui
(Continued)

FOREIGN PATENT DOCUMENTS

EP       2280759 B1   5/2015
WO   2003051457 A1   6/2003
(Continued)

OTHER PUBLICATIONS

Ginks et al., "Relationship between intracardiac impedance and left ventricular contractility in patients undergoing cardiac resynchronization", Europace, vol. 13, 984-991, 2001.
(Continued)

*Primary Examiner* — Erica S Lee
(74) *Attorney, Agent, or Firm* — Seager, Tufte & Wickhem LLP.

(57) ABSTRACT

A leadless cardiac pacemaker (LCP) is configured to sense cardiac activity and to pace a patient's heart and is disposable within a ventricle of the patient's heart. The LCP MAY include a housing, a first electrode and a second electrode that are secured relative to the housing and are spaced apart. A controller is disposed within the housing and is operably coupled to the first electrode and the second electrode such that the controller is capable of receiving, via the first electrode and the second electrode, electrical cardiac signals of the heart. The LCP may include a pressure sensor and/or an accelerometer. The controller may determine a pace time within a cardiac cycle based at least in part upon an indication of metabolic demand.

16 Claims, 16 Drawing Sheets

(51) Int. Cl.
*A61N 1/05* (2006.01)
*A61N 1/368* (2006.01)

(52) U.S. Cl.
CPC ..... *A61N 1/36564* (2013.01); *A61N 1/36578* (2013.01); *A61N 1/3756* (2013.01); *A61N 1/3682* (2013.01); *A61N 1/37512* (2017.08)

(56) References Cited

U.S. PATENT DOCUMENTS

| | | | |
|---|---|---|---|
| 7,212,861 B1 | 5/2007 | Park et al. |
| 7,286,875 B1 | 10/2007 | Park et al. |
| 7,580,746 B2 | 8/2009 | Gilkerson et al. |
| 7,596,412 B1 | 9/2009 | Kroll |
| 7,630,763 B2 | 12/2009 | Kwok et al. |
| 7,676,266 B1 | 3/2010 | Kroll |
| 7,702,389 B2 | 4/2010 | Czygan et al. |
| 7,702,392 B2 | 4/2010 | Echt et al. |
| 8,306,621 B2 | 11/2012 | Kim et al. |
| 8,478,400 B2 | 7/2013 | Hettrick et al. |
| 8,521,265 B2 | 8/2013 | Vollkron et al. |
| 8,527,068 B2 | 9/2013 | Ostroff |
| 8,831,721 B2 | 9/2014 | Hettrick et al. |
| 8,843,198 B2 | 9/2014 | Lian et al. |
| 9,174,062 B2 | 11/2015 | Stadler et al. |
| 9,199,086 B2 | 12/2015 | Zielinski et al. |
| 9,265,954 B2 | 2/2016 | Ghosh |
| 9,265,955 B2 | 2/2016 | Ghosh |
| 2001/0012953 A1 | 8/2001 | Molin et al. |
| 2001/0021864 A1 | 9/2001 | Molin |
| 2001/0031995 A1 | 10/2001 | Molin |
| 2001/0034540 A1 | 10/2001 | Molin |
| 2001/0049543 A1 | 12/2001 | Kroll |
| 2002/0087089 A1 | 7/2002 | Ben-Haim |
| 2003/0204212 A1 | 10/2003 | Burnes et al. |
| 2004/0172077 A1 | 9/2004 | Chinchoy |
| 2005/0038481 A1 | 2/2005 | Chinchoy et al. |
| 2005/0182447 A1 | 8/2005 | Schecter |
| 2007/0055170 A1 | 3/2007 | Lipped et al. |
| 2007/0060961 A1 | 3/2007 | Echt et al. |
| 2008/0195167 A1 | 8/2008 | Ryan |
| 2008/0269816 A1 | 10/2008 | Prakash et al. |
| 2010/0069768 A1 | 3/2010 | Min et al. |
| 2010/0113945 A1 | 5/2010 | Ryan |
| 2010/0198288 A1 | 8/2010 | Ostroff |
| 2010/0305640 A1* | 12/2010 | Bjorling ............... A61N 1/3622 607/17 |
| 2011/0160787 A1 | 6/2011 | Greenhut et al. |
| 2012/0136406 A1 | 5/2012 | Min |
| 2012/0165692 A1 | 6/2012 | Hollmark et al. |
| 2013/0079839 A1 | 3/2013 | Lian et al. |
| 2014/0277240 A1 | 9/2014 | Maskara et al. |
| 2015/0202443 A1 | 7/2015 | Zielinski et al. |
| 2015/0360036 A1* | 12/2015 | Kane ................. A61N 1/36585 607/18 |
| 2015/0367135 A1 | 12/2015 | Whittington et al. |
| 2016/0023000 A1* | 1/2016 | Cho .................... A61N 1/36578 607/18 |
| 2016/0059024 A1 | 3/2016 | Stahmann et al. |
| 2016/0067490 A1 | 3/2016 | Carney et al. |
| 2016/0113536 A1* | 4/2016 | Greenhut ............. A61B 5/7282 600/483 |
| 2017/0274213 A1* | 9/2017 | Ghosh ................ A61N 1/36585 |

FOREIGN PATENT DOCUMENTS

| | | |
|---|---|---|
| WO | 2004078254 A2 | 9/2004 |
| WO | 2005018740 A1 | 3/2005 |
| WO | 2007033094 A2 | 10/2007 |
| WO | 2009131768 A1 | 10/2009 |
| WO | 2010088687 A1 | 8/2010 |
| WO | 2014178035 A1 | 11/2014 |

OTHER PUBLICATIONS

MPVS Ultra, "Complete PV Loop Analysis", Pressure-Volume Loop Systems, Millar, downloaded Nov. 2017.

Roest et al., "Prediction of long-term outcome of cardiac resynchronization therapy by acute pressure-volume loop mesurments", European Journal of Heart Failure, 15, 299-307, 2013.

* cited by examiner

METHOD AND SYSTEM FOR DETERMINING A CARDIAC CYCLE PACE TIME IN ACCORDANCE WITH METABOLIC DEMAND IN A LEADLESS CARDIAC PACEMAKER SYSTEM

CROSS REFERENCE TO RELATED APPLICATIONS

This application claims the benefit of U.S. Provisional Patent Application Ser. No. 62/364,599 filed on Jul. 20, 2016, the disclosure of which is incorporated herein by reference.

TECHNICAL FIELD

The present disclosure generally relates to implantable medical devices, and more particularly, to systems that use a leadless cardiac pacemaker for monitoring, pacing and/or defibrillating a patient's heart

BACKGROUND

Implantable medical devices are commonly used today to monitor a patient and/or deliver therapy to a patient. For example and in some instances, pacing devices are used to treat patients suffering from various heart conditions that may result in a reduced ability of the heart to deliver sufficient amounts of blood to a patient's body. Such heart conditions may lead to slow, rapid, irregular, and/or inefficient heart contractions. To help alleviate some of these conditions, various medical devices (e.g., pacemakers, defibrillators, etc.) can be implanted in a patient's body. Such devices may monitor and in some cases provide electrical stimulation (e.g. pacing, defibrillation, etc.) to the heart to help the heart operate in a more normal, efficient and/or safe manner. In some cases, it is beneficial to sense and/or pace two or more chambers of the heart, such as to provide cardiac resynchronization therapy (CRT).

SUMMARY

This disclosure generally relates to implantable medical devices, and more particularly, to systems that use a leadless cardiac pacemaker for monitoring, pacing and/or defibrillating a patient's heart. In an example of the disclosure, a leadless cardiac pacemaker (LCP) is configured to sense cardiac activity and to pace a patient's heart and is disposable within a ventricle of the patient's heart. The LCP includes a housing, a first electrode that is secured relative to the housing and a second electrode that is secured relative to the housing and is spaced from the first electrode. A controller is disposed within the housing and is operably coupled to the first electrode and the second electrode. A first sensor is disposed relative to the housing and operably coupled to the controller, the controller being configured to receive a first sensor signal from the first sensor, the first sensor signal being responsive to an atrial contraction of the patient's heart. A second sensor is disposed relative to the housing and is operably coupled to the controller, the controller configured to receive a second sensor signal from the second sensor, the second sensor signal being responsive to an atrial contraction of the patient's heart. The controller may be configured to determine a ventricle pace time for delivering a ventricle pacing pulse to the ventricle of the patient's heart, the controller determining the ventricle pace time based at least in part on an indication of an atrial contraction event of the patient's heart and an indication of metabolic demand on the patient's heart. The indication of an atrial contraction event may be based primarily or exclusively on the received first signal if the indication of metabolic demand is below a metabolic demand threshold and primarily or exclusively on the received second signal if the indication of metabolic demand is above the metabolic demand threshold. The controller may be configured to generate and deliver a ventricle pacing pulse at the ventricle pace time.

Alternatively or additionally to any of the embodiments above, the first sensor may include an accelerometer.

Alternatively or additionally to any of the embodiments above, the second sensor may include a pressure sensor.

Alternatively or additionally to any of the embodiments above, the indication of metabolic demand may be based at least in part upon the received first sensor signal.

Alternatively or additionally to any of the embodiments above, the indication of metabolic demand may be based at least in part upon the received second sensor signal.

Alternatively or additionally to any of the embodiments above, the indication of metabolic demand may be based at least in part upon the received electrical cardiac signal.

Alternatively or additionally to any of the embodiments above, the first sensor or the second sensor includes an accelerometer, and the controller is configured to determine a posture of the patient based at least in part on an accelerometer signal from the accelerometer, and then to determine the indication of metabolic demand based at least in part on the determined posture.

Alternatively or additionally to any of the embodiments above, the first sensor or the second sensor includes an accelerometer, and the controller is configured to determine an activity level of the patient based at least in part on an accelerometer signal from the accelerometer, and then to determine the indication of metabolic demand based at least in part on the determined activity level.

Alternatively or additionally to any of the embodiments above, the first sensor and the second sensor include an accelerometer and a pressure sensor, and the controller is configured to attempt to detect an A-wave via a pressure signal from the pressure sensor and to determine the ventricle pace time based at least in part on the A-wave when the A-wave is detected. The controller is configured to determine the ventricle pace time based at least in part on one or more of a received pressure signal from the pressure sensor and/or a received accelerometer signal from the accelerometer other than the A-wave when the A-wave is not detected.

Alternatively or additionally to any of the embodiments above, the first sensor and the second sensor include an accelerometer and a pressure sensor, and the controller is configured to determine the ventricle pace time based at least in part on an LV pressure parameter indicated in a pressure signal of the pressure sensor when the indication of metabolic demand is above the metabolic demand threshold and to determine the ventricle pace time based at least in part on a heart sound indicated in the pressure signal of the pressure sensor and/or in an accelerometer signal of the accelerometer when the indication of metabolic demand is below the metabolic demand threshold.

Alternatively or additionally to any of the embodiments above, the first sensor or the second sensor includes a pressure sensor, and the controller is configured to determine the ventricle pace time to achieve a higher change rate in LV pressure over time (dP/dt) when the indication of metabolic demand is above a relaxation threshold and to determine the ventricle pace time to achieve a lower change rate in LV pressure over time (dP/dt) when the indication of metabolic demand is below the relaxation threshold.

Alternatively or additionally to any of the embodiments above, the controller may be configured to determine the ventricle pace time to achieve lower passive ventricular filling when the indication of metabolic demand is above a relaxation threshold and to determine the ventricle pace time to achieve higher passive ventricular filling when the indication of metabolic demand is below a relaxation threshold.

Alternatively or additionally to any of the embodiments above, the first sensor and the second sensor include an accelerometer and a pressure sensor, and the controller is configured to: detect an S2 heart sound via the pressure sensor and/or the accelerometer and to detect an A-wave via the pressure sensor. The controller may be configured to determine the ventricle pace time to achieve a smaller S2 to A-wave interval when the indication of metabolic demand exceeds a relaxation threshold and to determine the ventricle pace time to achieve a larger S2 to A-wave interval when the indication of metabolic demand does not exceed the relaxation threshold.

Alternatively or additionally to any of the embodiments above, the first sensor and the second sensor include an accelerometer and a pressure sensor and the controller is configured to detect an S2 heart sound via the pressure sensor and/or the accelerometer and to detect an S1 heart sound via the pressure sensor and/or the accelerometer. The controller may be configured to determine the ventricle pace time to achieve a smaller S2 to S1 interval when the indication of metabolic demand exceeds a relaxation threshold and to determine the ventricle pace time to achieve a larger S2 to S1 interval when the indication of metabolic demand does not exceed the relaxation threshold.

In another example of the disclosure, a leadless cardiac pacemaker (LCP) is configured to sense cardiac activity and to pace a patient's heart and is disposable within a ventricle of the patient's heart. The LCP includes a housing, a first electrode that is secured relative to the housing and a second electrode that is secured relative to the housing and is spaced from the first electrode. A controller is disposed within the housing and is operably coupled to the first electrode and the second electrode. A pressure sensor is disposed relative to the housing and is operably coupled to the controller, the controller configured to receive a pressure sensor signal from the pressure sensor that is responsive to an atrial contraction of the patient's heart. An accelerometer is disposed relative to the housing and is operably coupled to the controller, the controller configured to receive an accelerometer signal from the accelerometer that is responsive to an atrial contraction of the patient's heart. The controller is configured to determine a ventricle pace time for delivering a ventricle pacing pulse to the ventricle of the patient's heart, the controller determining the ventricle pace time based at least in part on an indication of an atrial contraction event of the patient's heart and an indication of a current posture of the patient, wherein the indication of an atrial contraction event is based primarily or exclusively on the received accelerometer signal if the indication of the posture of the patient is reclined, and is based primarily or exclusively on the received pressure signal if the indication of the posture of the patient is upright. The controller is configured to generate and deliver a ventricle pacing pulse at the ventricle pace time.

Alternatively or additionally to any of the embodiments above, the controller may be configured to determine the indication of the posture of the patient based at least in part on the accelerometer signal.

Alternatively or additionally to any of the embodiments above, the controller may be configured to determine the ventricle pace time based at least in part on an LV pressure parameter indicated in the pressure sensor signal when the indication of the posture of the patient is upright and to determine the ventricle pace time based at least in part on a heart sound indicated in the pressure sensor signal and/or in the accelerometer signal when the indication of the posture of the patient is reclined.

Alternatively or additionally to any of the embodiments above, the controller may be configured to determine the ventricle pace time to achieve lower passive ventricular filling when the indication of the posture of the patient is upright and to determine the ventricle pace time to achieve higher passive ventricular filling when the indication of the posture of the patient is reclined.

In another example of the disclosure, a method for determining a ventricle pace time in a patient using a leadless cardiac pacemaker (LCP) implanted in the patient's left ventricle and including a pressure sensor includes determining or receiving an indication of metabolic demand. A ventricle pace time may be determined to achieve lower passive ventricular filling when the indication of metabolic demand exceeds a threshold and to achieve higher passive ventricular filling when the indication of metabolic demand does not exceed the threshold.

Alternatively or additionally to any of the embodiments above, a measure of the passive ventricular filling is based, at least in part on, a pressure signal from the pressure sensor.

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which.

Figure 1:
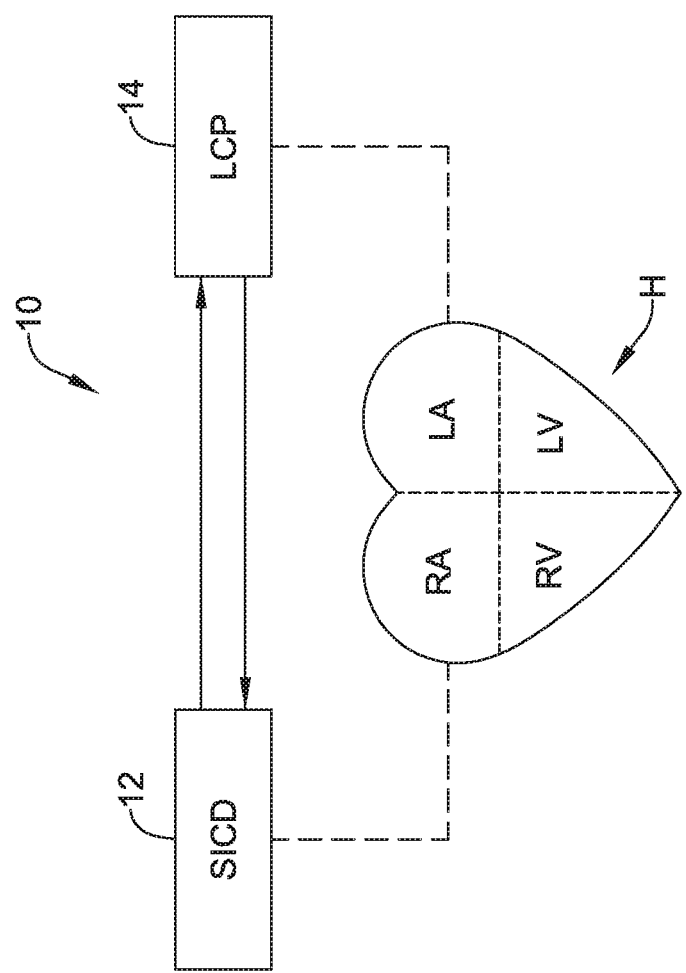
FIG. 1 is a highly schematic diagram of an illustrative system in accordance with an example of the disclosure.

While the disclosure is amenable to various modifications and alternative forms, specifics thereof have been shown by way of example in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure.

All numbers are herein assumed to be modified by the term "about", unless the content clearly dictates otherwise. The recitation of numerical ranges by endpoints includes all numbers subsumed within that range (e.g., 1 to 5 includes 1, 1.5, 2, 2.75, 3, 3.80, 4, and 5).

As used in this specification and the appended claims, the singular forms "a", "an", and "the" include the plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is contemplated that the feature, structure, or characteristic may be applied to other embodiments whether or not explicitly described unless clearly stated to the contrary.

A normal, healthy heart induces contraction by conducting intrinsically generated electrical signals throughout the heart. These intrinsic signals cause the muscle cells or tissue of the heart to contract in a coordinated manner. These contractions forces blood out of and into the heart, providing circulation of the blood throughout the rest of the body. Many patients suffer from cardiac conditions that affect the efficient operation of their hearts. For example, some hearts develop diseased tissue that no longer generate or efficiently conduct intrinsic electrical signals. In some examples, diseased cardiac tissue may conduct electrical signals at differing rates, thereby causing an unsynchronized and inefficient contraction of the heart. In other examples, a heart may generate intrinsic signals at such a low rate that the heart rate becomes dangerously low. In still other examples, a heart may generate electrical signals at an unusually high rate, even resulting in cardiac fibrillation. Implantable medical device are often used to treat such conditions by delivering one or more types of electrical stimulation therapy to the patient's heart.

FIG. 1 is a schematic diagram showing an illustrative system 10 that may be used to sense and/or pace a heart H. In some cases, the system 10 may also be configured to be able to shock the heart H. The heart H includes a right atrium RA and a right ventricle RV. The heart H also includes a left atrium LA and a left ventricle LV. In some cases, the illustrative system 10 includes an SICD (subcutaneous implantable cardioverter defibrillator) 12. While not shown in this Figure, in some cases the SICD 12 may include a lead that may be configured to be placed subcutaneously relative to a patient's sternum and outside of the patient's heart. In some cases, the lead may extend around or through the sternum and may be fixed adjacent an inner surface of the sternum and outside of the patient's heart. The SICD 12 may be configured to sense electrical activity generated by the heart H as well as provide electrical energy to the heart H in order to shock the heart H from an undesired heart rhythm to a desired heart rhythm.

In some cases, the system 10 may include an LCP 14 that may be configured to sense and/or pace the heart H. While a single LCP 14 is illustrated, it will be appreciated that two or more LCPs 14 may be implanted in or on the heart H. The LCP 14 may be implanted into any chamber of the heart, such as the right atrium RA, the left atrium LA, the right ventricle RV and the left ventricle LV. When more than one LCP is provided, each LCP may be implanted in a different chamber. In some cases, multiple LCP's may be implanted within a single chamber of the heart H.

In some cases, the SICD 12 and the LCP 14 may be implanted at the same time. In some instances, depending on the cardiac deficiencies of a particular patient, the SICD 12 may be implanted first, and one or more LCPs 14 may be implanted at a later date if/when the patient's heart decompensates and it becomes necessary to pace the heart H. In some cases, it is contemplated that one or more LCPs 14 may be implanted first, in order to sense and pace the heart H. When a need for possible defibrillation becomes evident, the SICD 12 may subsequently be implanted. Regardless of implantation order or sequence, it will be appreciated that the SICD 12 and the LCP 14 may communicate with each other using any desired communications protocol, such as conducted communication through the patient's body.

Figure 2:
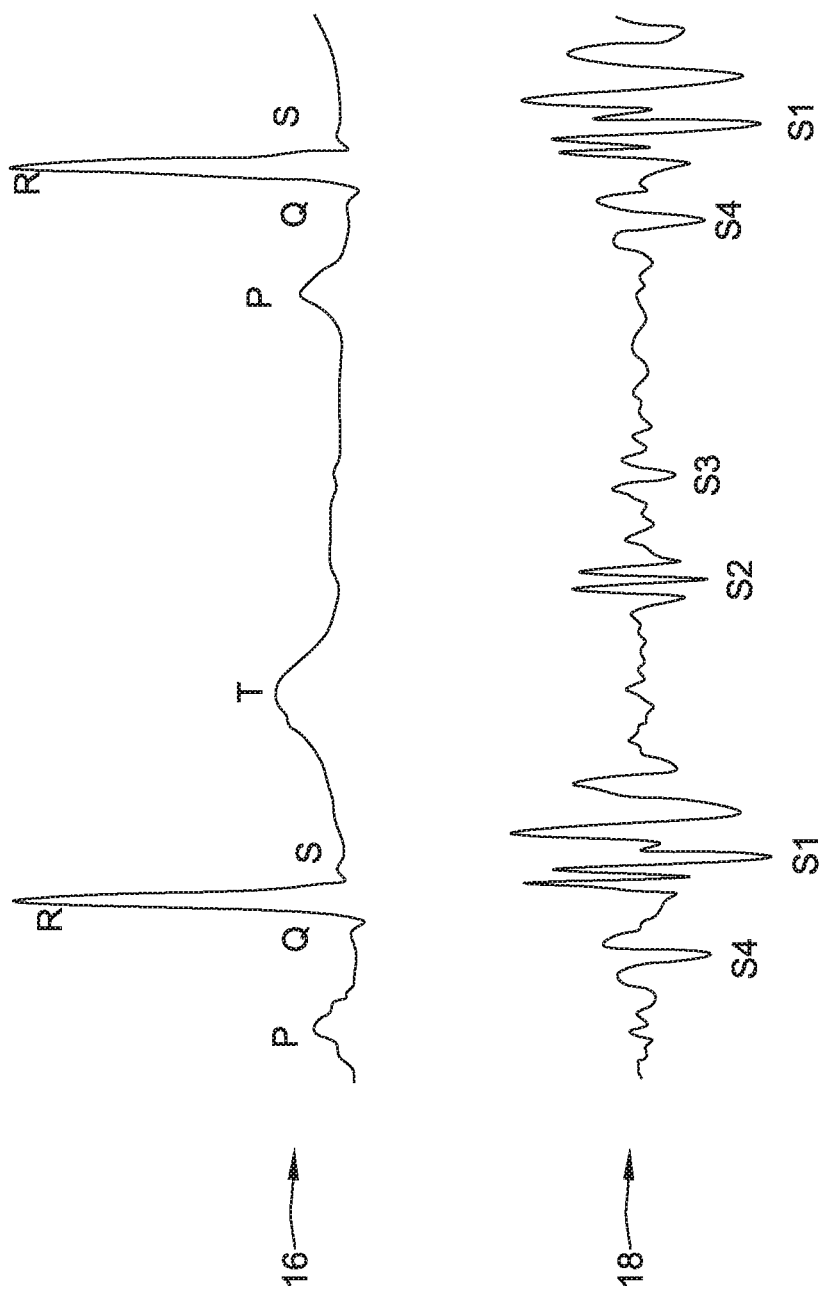
FIG. 2 is a graphical representation of an electrocardiogram (ECG) showing a temporal relationship between electrical signals of the heart and mechanical indications of contraction of the heart.

With reference to FIG. 2, it will be appreciated that the heart H is controlled via electrical signals that pass through the cardiac tissue and that can be detected by implanted devices such as but not limited to the SICD 12 and/or the LCP 14 of FIG. 1. FIG. 2 includes a portion of an electrocardiogram (ECG) 16 along with a heart sounds trace 18. As can be seen in the ECG 16, a heartbeat includes a P-wave that indicates atrial depolarization. A QRS complex, including a Q-wave, an R-wave and an S-wave, represents ventricular depolarization. A T-wave indicates repolarization of the ventricles. It will be appreciated that the ECG 16 may be detected by implanted devices such as but not limited to the SICD 12 and/or the LCP 14 of FIG. 1.

A number of heart sounds may also be detectable while the heart H beats. It will be appreciated that the heart sounds may be considered as on example of mechanical indications of the heart beating. Other illustrative mechanical indications may include, for example, endocardial acceleration or movement of a heart wall detected by an accelerometer in the LCP, acceleration or movement of a heart wall detected by an accelerometer in the SICD, a pressure, pressure change, or pressure change rate in a chamber of the heart H detected by a pressure sensor of the LCP, acoustic signals caused by heart movements detected by an acoustic sensor (e.g. accelerometer, microphone, etc.) and/or any other suitable indication of a heart chamber beating.

An electrical signal typically instructs a portion of the heart H to contract, and then there is a corresponding mechanical indication. In some cases, there may be a first heart sound that is denoted S1 and that is produced by vibrations generated by closure of the mitral and tricuspid valves during a ventricle contraction, a second heart sound that is denoted S2 and that is produced by closure of the aortic and pulmonary valves, a third heart sound that is denoted S3 and that is an early diastolic sound caused by the rapid entry of blood from the right atrium RA into the right ventricle RV and from the left atrium LA into the left ventricle LV, and a fourth heart sound that is denoted S4 and that is a late diastolic sound corresponding to late ventricular filling during an active atrial contraction.

Because the heart sounds are a result of cardiac muscle contracting or relaxing in response to an electrical signal, it will be appreciated that there is a delay between the electrical signal, indicated by the ECG 16, and the corresponding mechanical indication, indicated in the example shown by the heart sounds trace 18. For example, the P-wave of the ECG 16 is an electrical signal triggering an atrial contraction. The S4 heart sound is the mechanical signal caused by the atrial contraction. In some cases, it may be possible to use this relationship between the P-wave and the S4 heart sound. For example, if one of these signals may be detected, the relationship can be used as a timing mechanism to help search for the other. For example, if the P-wave can be detected, a window following the P-wave can be defined and searched in order to find and/or isolate the corresponding S4 heart sound. In some cases, detection of both signals may be an indication of an increased confidence level in a detected atrial contraction. In some cases, detection of either signal may be sufficient to identify an atrial contraction. The identity of an atrial contraction may be used to identify an atrial contraction timing fiducial (e.g. a timing marker of the atrial contraction).

Figure 3:
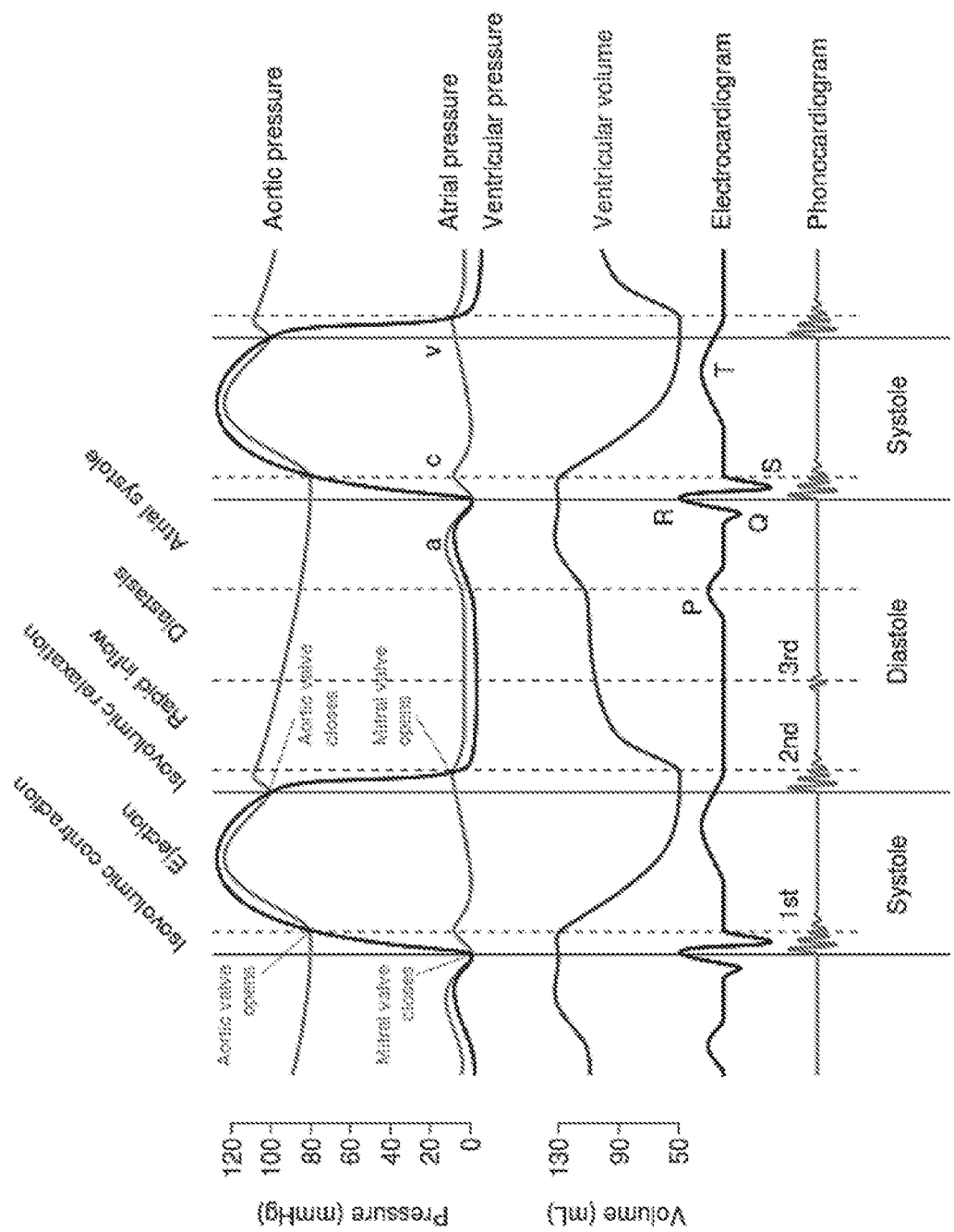
FIG. 3 is a graph showing example pressures and volumes within the heart over time.

In some cases, the relationship of certain electrical signals and/or mechanical indications may be used to predict the timing of other electrical signals and/or mechanical indications within the same heartbeat. Alternatively, or in addition, the timing of certain electrical signals and/or mechanical indications corresponding to a particular heartbeat may be used to predict the timing of other electrical signals and/or mechanical indications within a subsequent heartbeat. It will be appreciated that as the heart H undergoes a cardiac cycle, the blood pressures and blood volumes within the heart H will vary over time. FIG. 3 illustrates how these parameters match up with the electrical signals and corresponding mechanical indications.

FIG. 3 is a graph showing example pressures and volumes within a heart over time. More specifically, FIG. 3 shows an illustrative example of the aortic pressure, left ventricular pressure, left atrial pressure, left ventricular volume, an electrocardiogram (ECG or egram), and heart sounds of the heart H over two consecutive heart beats. A cardiac cycle may begin with diastole, and the mitral valve opens. The ventricular pressure falls below the atrial pressure, resulting in the ventricular filling with blood. During ventricular filling, the aortic pressure slowly decreases as shown. During systole, the ventricle contracts. When ventricular pressure exceeds the atrial pressure, the mitral valve closes, generating the S1 heart sound. Before the aortic valve opens, an isovolumetric contraction phase occurs where the ventricle pressure rapidly increases but the ventricle volume does not significantly change. Once the ventricular pressure equals the aortic pressure, the aortic valve opens and the ejection phase begins where blood is ejected from the left ventricle into the aorta. The ejection phase continues until the ventricular pressure falls below the aortic pressure, at which point the aortic valve closes, generating the S2 heart sound. At this point, the isovolumetric relaxation phase begins and ventricular pressure falls rapidly until it is exceeded by the atrial pressure, at which point the mitral valve opens and the cycle repeats. Cardiac pressure curves for the pulmonary artery, the right atrium, and the right ventricle, and the cardiac volume curve for the right ventricle, may be similar to those illustrated in FIG. 3. In many cases, the cardiac pressure in the right ventricle is lower than the cardiac pressure in the left ventricle.

Figure 4:
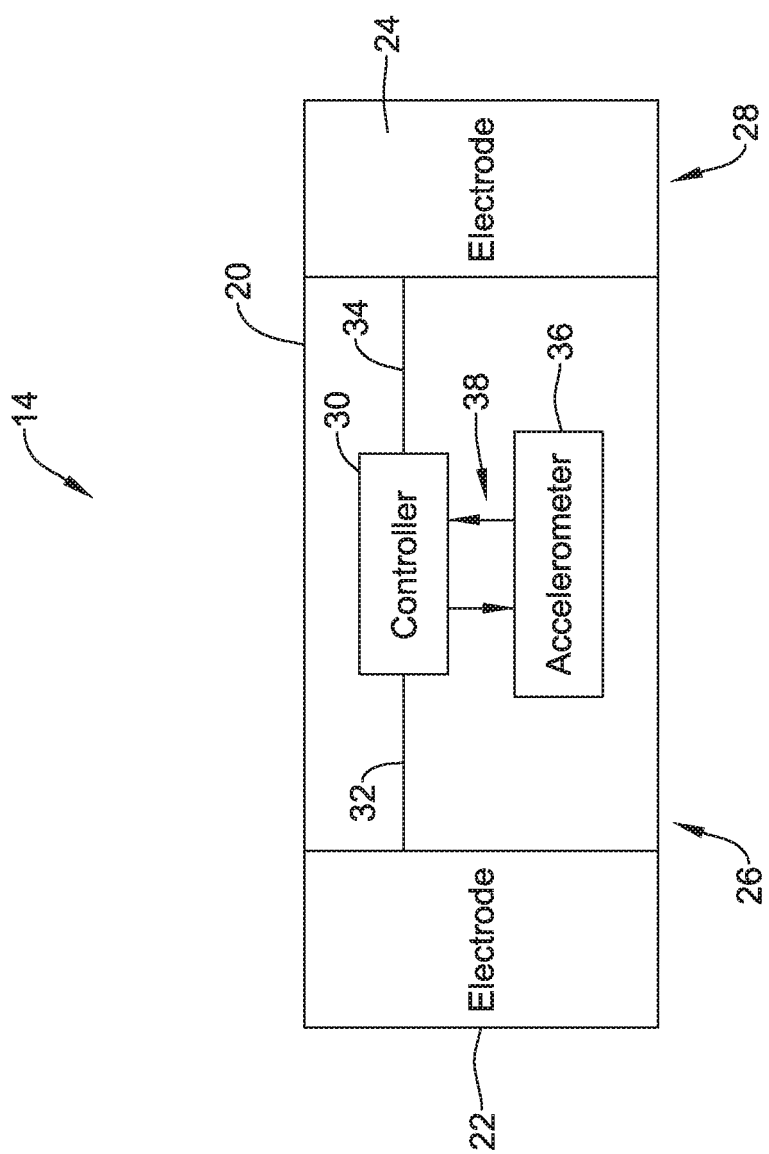
FIG. 4 is a schematic block diagram of an illustrative leadless cardiac pacemaker (LCP) useable in the system of FIG. 1.

FIG. 4 is a schematic diagram of an illustrative LCP 14. In some cases, as indicated, the LCP 14 may be considered as being configured to sense cardiac activity and to pace a patient's heart H. In some cases, the LCP 14 may be disposable within a ventricle of the heart H, such as the right ventricle RV or the left ventricle LV. The LCP 14 may be considered as including a housing 20, a first electrode 22 that is secured relative to the housing 20 and exposed to an environment outside the housing 20 (e.g. blood, tissue, etc.), and a second electrode 24 that is secured relative to the housing 20 and exposed to the environment outside of the housing 20 (e.g. blood, tissue, etc.). The second electrode 24 may be spaced from the first electrode 22. In some cases, as illustrated, the first electrode 22 may be disposed at or near a first end 26 of the housing 20 and the second electrode 24 may be disposed at or near a second end 28 of the housing 20, although this is not required in all cases.

The LCP 14 may further include a controller 30 that is disposed within the housing 20 and that is operably coupled to the first electrode 22 via a first electrical connection 32 and the second electrode 24 via a second electrical connection 34. In some cases, the controller 30 may be capable of receiving, via the first electrode 22 and the second electrode 24, electrical signals that include an electrical indication of an atrial (or other) contraction (e.g. a P-wave of an ECG 16, see FIG. 2). In some cases, the controller 30 may receive electrical signals (e.g. conducted communication signals) that include an indication of atrial (or other) contractions from a remote device such as the SICD 12 (FIG. 1). In some cases, the controller 30 may also be configured to determine an atrial contraction timing fiducial based at least in part upon a sensed indication of atrial contraction in a first heartbeat and/or a sensed indication of ventricular contraction in the first heartbeat, an immediately preceding heartbeat and/or an immediately succeeding heartbeat. In some cases, the controller 30 may be configured to generate and deliver a ventricle pacing pulse using the atrial contraction timing fiducial (e.g. after an A-V delay).

In some cases, the LCP 14 may include an accelerometer 36 that is disposed within the housing 20 and that is operably coupled to the controller 30 via electrical connections 38. In some cases, as discussed further with respect to subsequent Figures, the LCP 14 may include an optional pressure sensor. In some cases, the controller 30 may be configured to detect, via a signal from the accelerometer 36, a mechanical indication of atrial (or other) contraction. In some cases, the mechanical indication of atrial contraction may include but is not limited to an S4 heart sound. While the LCP 14 is shown as including an accelerometer, it will be appreciated that other sensors may be able to provide a signal representing a mechanical indication of atrial (or other) contraction. For example, in some cases the LCP 14 may include a microphone. In some cases, the LCP 14 may include a sonomicrometer, a cardiomechanical sensor that includes, for example, embedded piezoelectric material, or other piezoelectric sensors. In some cases, the LCP may include a pressure sensor for sensing an indication of atrial contraction. These are just examples.

In some cases, signals that provide an indication of atrial contraction may include one or more of an S3 heart sound signal, an S4 heart sound signal, an A-wave signal and/or a P-wave signal. In some cases, signals that provide an indication of ventricular contraction may include one or more of a pulse pressure signal, a dP/dt signal, an R-wave to R-wave interval, a QRS complex width, and/or a ventricle pressure-volume loop parameter. These are just some examples.

Figure 5:
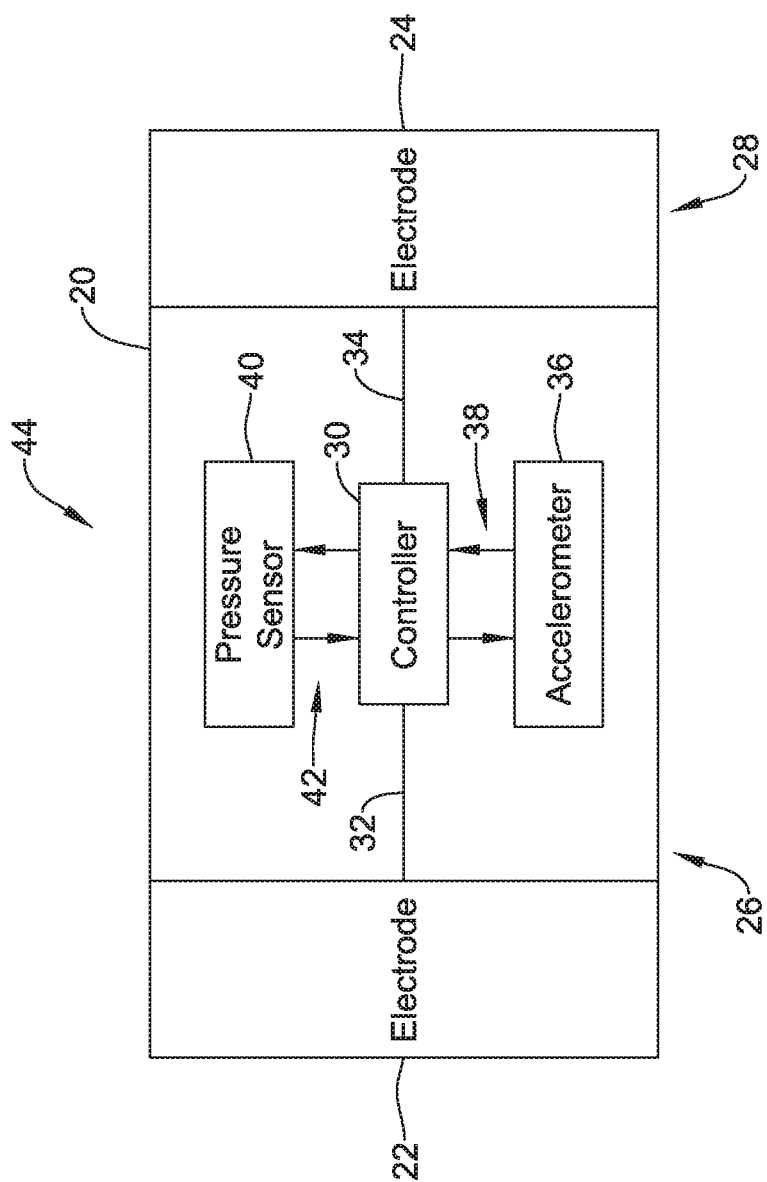
FIG. 5 is a schematic block diagram of an illustrative leadless cardiac pacemaker (LCP) useable in the system of FIG. 1.

FIG. 5 is a schematic diagram of an illustrative LCP 44. In some cases, as indicated, the LCP 44 may be considered as being configured to sense cardiac activity and to pace a patient's heart H. In some cases, the LCP 44 may be disposable within a ventricle of the heart H, such as the right ventricle RV or the left ventricle LV. The LCP 44 may be considered as including a housing 20, a first electrode 22 that is secured relative to the housing 20 and exposed to an environment outside the housing 20 (e.g. blood, tissue, etc.), and a second electrode 24 that is secured relative to the housing 20 and exposed to the environment outside of the housing 20 (e.g. blood, tissue, etc.). The second electrode 24 may be spaced from the first electrode 22. In some cases, as illustrated, the first electrode 22 may be disposed at or near a first end 26 of the housing 20 and the second electrode 24 may be disposed at or near a second end 28 of the housing 20, although this is not required in all cases.

The LCP 14 may further include a controller 30 that is disposed within the housing 20 and that is operably coupled to the first electrode 22 via a first electrical connection 32 and the second electrode 24 via a second electrical connection 34. In some cases, the controller 30 may be capable of receiving, via the first electrode 22 and the second electrode 24, electrical signals that include an electrical indication of an atrial (or other) contraction (e.g. a P-wave of an ECG 16, see FIG. 2). In some cases, detecting a far-field P-wave via the electrodes 22 and 24 of an LCP implanted in the ventricle may have a relatively low signal-to-noise ratio. Detecting the P-wave using the SICD lead may have a higher signal to noise ratio. In some cases, the controller 30 may receive electrical signals (e.g. conducted communication signals) that include an indication of atrial (or other) contractions from a remote device such as the SICD 12 (FIG. 1).

In some cases, the LCP 44 may include an accelerometer 36 that is disposed within the housing 20 and that is operably coupled to the controller 30 via electrical connections 38. In some cases, the LCP 44 may also include a pressure sensor 40 that is disposed within the housing 20 and that is operably coupled to the controller 30 via electrical connections 42. In some instances, a pressure sensor signal may be responsive to an atrial contraction of the patient's heart. Likewise an accelerometer signal may be responsive to an atrial contraction of the patient's heart.

In some cases, the pressure signal may be used to determine a number of parameters. For example, the pressure signal may be used to determine or detect an A-wave (atrial kick). In another example, the pressure signal may be used to determine or detect a pressure pulse or pressure vibrations associated with S4, which may, for example, be in the 25-30 Hz range. In some cases, the S4 heart sound may be easier to detect using the pressure signal than the accelerometer signal, particularly since the ventricle pressure is not changing substantially at this time (ventricle is filling). In another example, the pressure signal may be used to determine a change in ventricle pressure relative to time (dP/dt).

In some cases, the controller 30 may be configured to detect, via a signal from the accelerometer 36, one or more signals indicating an atrial (or other) contraction. In some cases, the signal received from the accelerometer 36 may include a heart sound signal (e.g. S4) or an endocardial acceleration signal. While the LCP 14 is shown as including an accelerometer 36 and a pressure sensor 40, it will be appreciated that other sensors may also be able to provide a signal representing a mechanical indication of atrial (or other) contraction. For example, in some cases the LCP 14 may include a microphone. In some cases, the LCP 44 may include a sonomicrometer, a cardiomechanical sensor that includes, for example, embedded piezoelectric material, or other piezoelectric sensors. These are just examples.

In some cases, the controller 30 may also be configured determine an atrial contraction timing fiducial based at least in part upon two or more of a signal received from the pressure sensor 40, a signal received from the accelerometer 36 (e.g. representing a heart sound and/or endocardial acceleration), and an electrical cardiac signal received via the first electrode 22 and the second electrode 24. In some cases, the electrical cardiac signal received via the first electrode 22 and the second electrode 24 may include at least a portion of an electrocardiogram (ECG). In some cases, the electrical cardiac signal received via the first electrode 22 and the second electrode 24 may include a P-wave. In some instances, the electrical cardiac signal received via the first electrode 22 and the second electrode 24 may include a QRS complex, from which a QRS width can be determined. In some cases, the electrical cardiac signal received via the first electrode 22 and the second electrode 24 may include two consecutive R waves, from which an R-wave to R-wave interval can be determined. In some cases, the electrical cardiac signal may include a conducted or other communicated electrical signal from another device (e.g. SICD device) that includes an indication of an atrial or other contraction of the heart H. In some cases, the controller 30 may be configured to generate and deliver a ventricle pacing pulse using the atrial contraction timing fiducial.

In some cases, the controller 30 may be configured to determine the atrial contraction timing fiducial based at least in part upon a signal received from the pressure sensor 40 and a signal received from the accelerometer 36. In some instances, the controller 30 may be configured to determine the atrial contraction timing fiducial based at least in part upon a signal received from the pressure sensor 40 and an electrical cardiac signal received via the first electrode 22 and the second electrode 24. In some cases, the controller 30 may be configured to determine the atrial contraction timing fiducial based at least in part upon a sensed A-wave in the signal received from the pressure sensor 40 and a sensed signal associated with an S4 heart sound in the signal received from the accelerometer 36.

In some instances, the controller 30 may be configured to determine a pace time for delivering a ventricle pacing pulse to the ventricle of the patient's heart H, and the controller 30 may determine the pace time based at least in part on a pressure signal received from the pressure sensor 40. For example, in some cases, the controller may be configured to determine the pace time based at least in part on the received pressure signal and the received accelerometer signal. As another example, in some cases, the controller 30 may be configured to determine the pace time based at least in part on a heart sound or endocardial acceleration represented in the received pressure signal and/or in the received accelerometer signal.

In some cases, the controller 30 may be configured to determine the pace time based at least in part on the received pressure signal and the received electrical cardiac signal. In some instances, the controller 30 may be configured to determine the pace time based at least in part on the received pressure signal, the received accelerometer signal and the received electrical cardiac signal. In some cases, the controller 30 may be configured to determine the pace time based at least in part on a diastolic pressure represented in the received pressure signal. In some cases, the controller 30 may be configured to determine the pace time based at least in part on an A-wave represented in the received pressure signal. In some instances, the controller 30 may be configured to determine the pace time based at least in part on a systolic pressure represented in the received pressure signal. In some cases, the controller 30 may be configured to determine the pace time based at least in part on a dP/dt parameter (e.g. pace at a time to maximize dP/dt in the ventricle) during systole represented in the received pressure signal. In some cases, the controller 30 may be configured to determine the pace time based at least in part on when the received pressure signal crossing a predetermined threshold during systole. In some instances, the controller 30 may be configured to determine the pace time based at least in part on an A-V delay relative to a previously determined atrial contraction timing fiducial, and the controller 30 may adjust the A-V delay based at least in part on one or more of the received pressure signal, the received accelerometer signal and the received electrical cardiac signal during the current, previous and/or subsequent cardiac cycles.

In some instances, the controller 30 may be configured to determine a ventricle pace time for delivering a ventricle pacing pulse to the ventricle of the patient's heart H. For example, in some cases, the controller 30 may determine the ventricle pace time based at least in part on an indication of an atrial contraction event of the patient's heart H and an indication of a current posture of the patient. It will be appreciated that cardiac demand, or the blood pumping needs of the patient, may vary depending on whether the patient is laying down, sitting, standing, etc. In some cases, for example, an indication of an atrial contraction event may be based primarily or exclusively on the received accelerometer signal if the indication of the posture of the patient is reclined, and may be based primarily or exclusively on the received pressure signal if the indication of the posture of the patient is upright. The signal-to-noise ratio may be greater for the accelerometer signal when the patient is at rest (e.g. reclined) and the signal-to-noise ratio may be greater for the pressure signal when the patient is active (e.g. upright). In some cases, the controller 30 may be configured to determine the indication of the posture of the patient based at least in part on the accelerometer signal.

In some instances, the controller 30 may be configured to determine the ventricle pace time based at least in part on an LV pressure parameter indicated in the pressure sensor signal when the indication of the posture of the patient is upright. The controller 30 may, conversely, be configured to determine the ventricle pace time based at least in part on a heart sound indicated in the pressure sensor signal and/or in the accelerometer signal when the indication of the posture of the patient is reclined. In some cases, the controller 30 may be configured to determine the ventricle pace time to achieve lower passive ventricular filling when the indication of the posture of the patient is upright and to determine the ventricle pace time to achieve higher passive ventricular filling when the indication of the posture of the patient is reclined (e.g. maximize diastolic interval, increase S2 to A-wave rise interval, lower heart rate, etc.). This may operate the heart in a manner that reduces stretch stress on the heart while still meeting the current metabolic demands of the patient during times when the metabolic demand is relative low (e.g. reclined), and to operate the heart in a manner that maximizes pumping capacity when the metabolic demand is higher (e.g. upright). This may help reduce the rate at which a patient's heart decompensates by allowing the heart to "rest" more during times of low metabolic demand. While posture may be used as an indicator for metabolic demand, it is contemplated that metabolic demand may be estimated based on any number of other parameters including, for example, heart rate, respiration of the patient, activity level of the patient, posture, blood gas, blood analytes (e.g. lactate or norepinephrine), cardiac conduction velocities (e.g. PR interval or QT interval) and/or sleep state.

Figure 6:
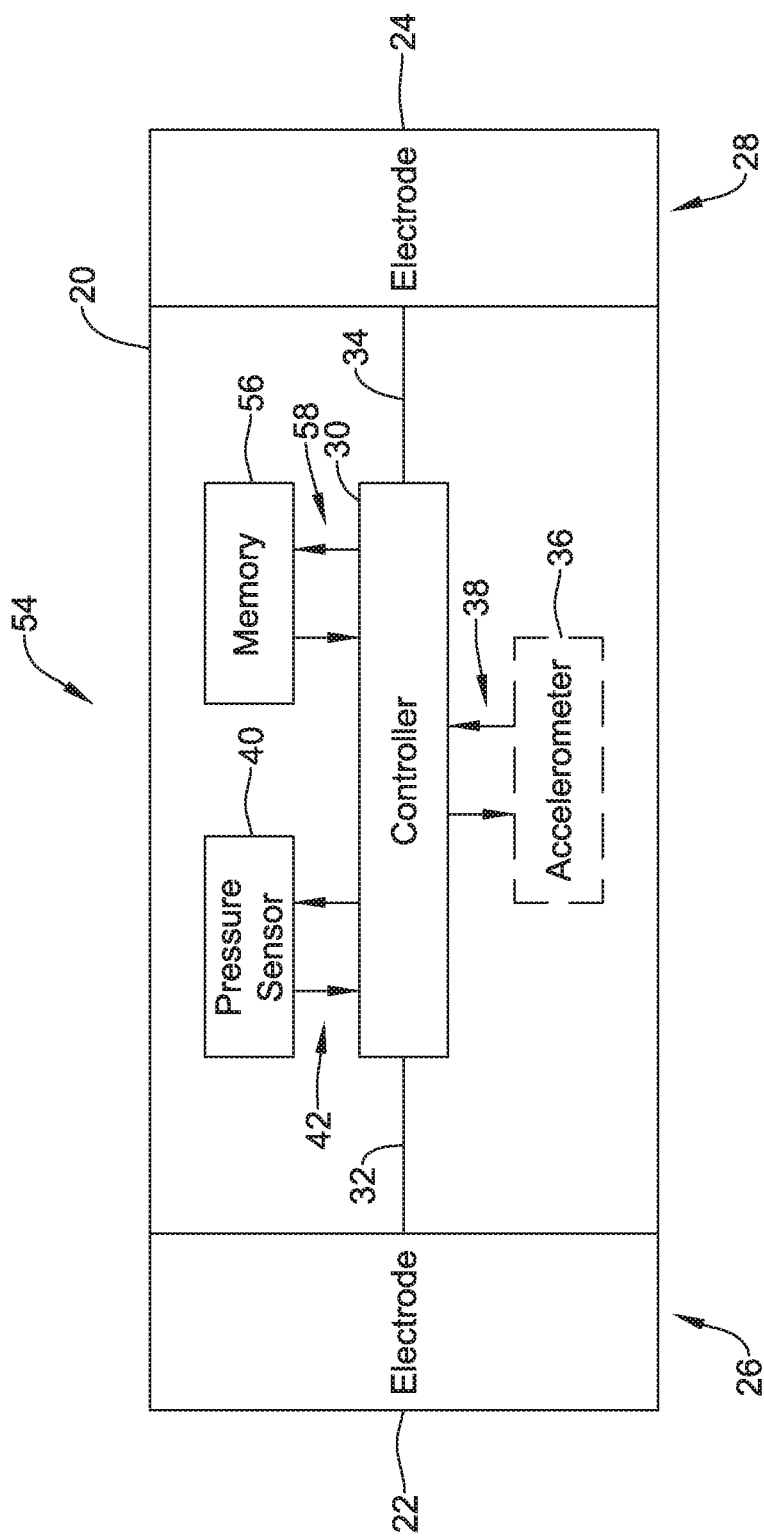
FIG. 6 is a schematic block diagram of an illustrative leadless cardiac pacemaker (LCP) useable in the system of FIG. 1.

FIG. 6 is a schematic diagram of an illustrative LCP 54. In some cases, as indicated, the LCP 54 may be considered as being configured to sense cardiac activity and to pace a patient's heart H. In some cases, the LCP 54 may be disposable within a ventricle of the heart H, such as the right ventricle RV or the left ventricle LV. The LCP 54 may be considered as including a housing 20, a first electrode 22 that is secured relative to the housing 20 and exposed to an environment outside the housing 20 (e.g. blood, tissue, etc.), and a second electrode 24 that is secured relative to the housing 20 and exposed to the environment outside of the housing 20 (e.g. blood, tissue, etc.). The second electrode 24 may be spaced from the first electrode 22. In some cases, as illustrated, the first electrode 22 may be disposed at or near a first end 26 of the housing 20 and the second electrode 24 may be disposed at or near a second end 28 of the housing 20, although this is not required in all cases.

The LCP 54 may further include a controller 30 that is disposed within the housing 20 and that is operably coupled to the first electrode 22 via a first electrical connection 32 and the second electrode 24 via a second electrical connection 34. In some cases, the controller 30 may be capable of receiving, via the first electrode 22 and the second electrode 24, electrical signals representative of cardiac activity. In some cases, the controller 30 may receive signals that include an electrical indication of an atrial (or other) contraction (e.g. a P-wave of an ECG 16, see FIG. 2). In some cases, the controller 30 may receive electrical signals (e.g. conducted communication signals) that include an indication of atrial (or other) contractions from a remote device such as the SICD 12 (FIG. 1).

In some cases, the LCP 54 may include a memory 56 that is operably coupled to the controller 30 via electrical connections 58. In some cases, for example, the memory 56 may be configured to store information pertaining to a previously determined atrial contraction timing fiducial, as well as other information.

In some cases, the LCP 54 may include an accelerometer 36 that is disposed within the housing 20 and that is operably coupled to the controller 30 via electrical connections 38. In some cases, the LCP 54 may further include a pressure sensor 40 that is disposed within the housing 20 and that is operably coupled to the controller 30 via electrical connections 42. The controller 30 may, for example, be configured to receive an accelerometer signal from the accelerometer 36 and/or a pressure sensor signal from the pressure sensor 40. In some instances, for example, the controller 30 may be configured to determine an A-V delay relative to a previously determined atrial contraction timing fiducial based at least in part on a pressure signal from the pressure sensor 40. In some cases, the controller 30 may be configured to adjust the A-V delay based at least in part on the accelerometer signal. In some cases, the controller 30 may be configured to generate a ventricle pacing pulse after the adjusted A-V delay following the previously determined atrial contraction timing fiducial.

In some instances, the pressure signal received by the controller 30 may include a pulse pressure, and the controller 30 may be configured to adjust the A-V delay relative to the previously determined atrial contraction timing fiducial based at least in part on the pulse pressure. In some cases, the pressure signal received by the controller 30 includes a rate of change in pressure over time (dP/dt) and the controller 30 may be configured to adjust the A-V delay relative to the previously determined atrial contraction timing fiducial based at least in part on the dP/dt. In some cases, the A-V delay may be adjusted to maximize the dP/dt sensed in the ventricle. In some cases, the A-V delay may be adjusted to minimize the negative dP/dt sensed in the ventricle in diastole. In some cases, the A-V delay may be adjusted to achieve a minimum ventricle pressure pulse width (e.g. width between maximum dP/dt and maximum negative dP/dt). In some cases, heart sounds in conjunction with the LV pressure waveform may be used to separate out various timing components of the heart H such as ejection time, isovolumetric contraction time, isovolumetric relation time, etc.)

In some instances, the pressure signal received by the controller 30 may include an A-wave signal, and the controller 30 may be configured to progressively reduce the A-V delay until the A-wave signal is not detected, and then progressively increase the A-V delay until the A-wave signal is again just detected and an onset of LV pressure rise is right on top of the A-wave, at which point the A-V delay may be considered to be optimal. In some cases, the controller 30 may be configured to adjust the A-V delay in response to an LV volume related impedance signal received or measured via the first electrode 22 and the second electrode 24, and the controller 30 may adjust the A-V delay relative to the previously determined atrial contraction timing fiducial in order to increase an LV ejection fraction that is estimated using the LV volume related impedance signal.

In some cases, the controller 30 may be configured to adjust the A-V delay in response to an electrical cardiac signal received via the first electrode 22 and the second electrode 24 including a QRS complex, from which a QRS width can be determined, and the controller 30 may be configured to adjust the A-V delay relative to the previously determined atrial contraction timing fiducial in order to minimize the QRS width. In some instances, the controller 30 may be configured to adjust the A-V delay in response to a received signal indicative of mitral regurgitation from the pressure sensor 40 and/or the accelerometer 36, and the controller 30 may be configured to adjust the A-V delay relative to the previously determined atrial contraction timing fiducial in order to minimize detected mitral regurgitation.

Figure 7:
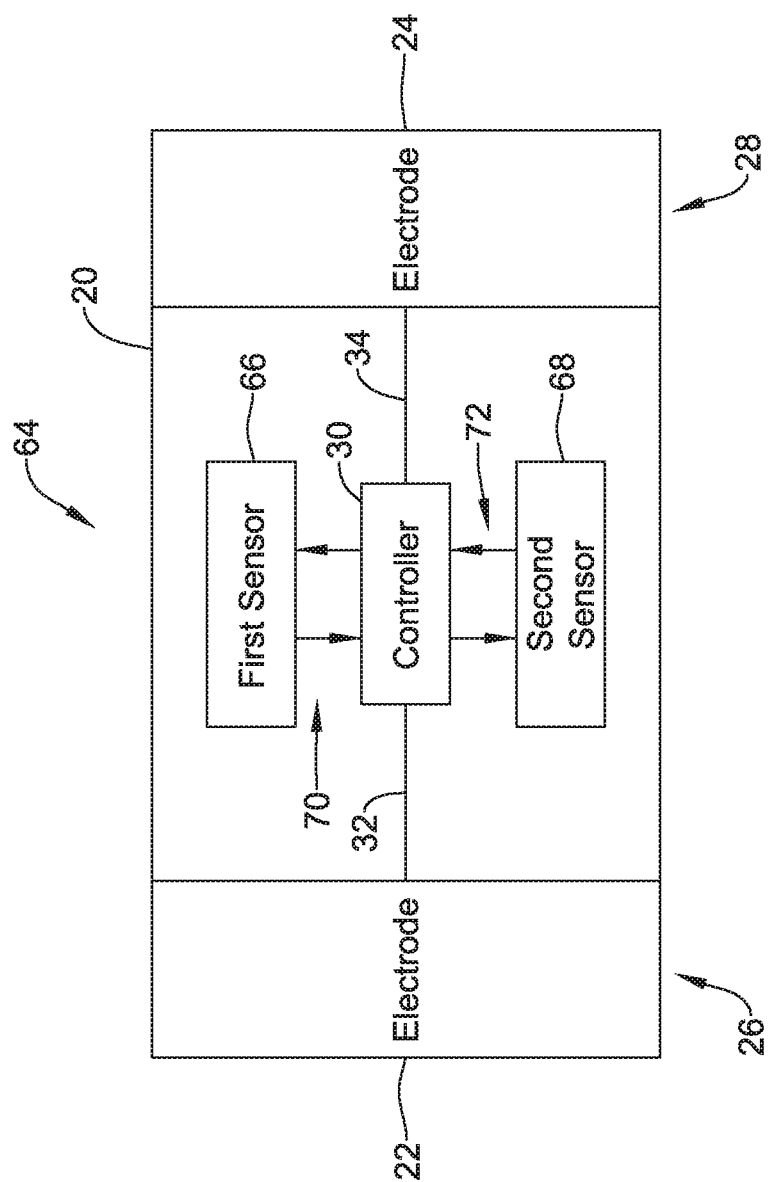
FIG. 7 is a schematic block diagram of an illustrative leadless cardiac pacemaker (LCP) useable in the system of FIG. 1.

FIG. 7 is a schematic diagram of an illustrative LCP 64. In some cases, as indicated, the LCP 64 may be considered as being configured to sense cardiac activity and to pace a patient's heart H. In some cases, the LCP 64 may be disposable within a ventricle of the heart H, such as the right ventricle RV or the left ventricle LV. The LCP 64 may be considered as including a housing 20, a first electrode 22 that is secured relative to the housing 20 and exposed to an environment outside the housing 20 (e.g. blood, tissue, etc.), and a second electrode 24 that is secured relative to the housing 20 and exposed to the environment outside of the housing 20 (e.g. blood, tissue, etc.). The second electrode 24 may be spaced from the first electrode 22. In some cases, as illustrated, the first electrode 22 may be disposed at or near a first end 26 of the housing 20 and the second electrode 24 may be disposed at or near a second end 28 of the housing 20, although this is not required in all cases.

The LCP 64 may further include a controller 30 that is disposed within the housing 20 and that is operably coupled to the first electrode 22 via a first electrical connection 32 and the second electrode 24 via a second electrical connection 34. In some cases, the controller 30 may be capable of receiving, via the first electrode 22 and the second electrode 24, electrical signals representative of cardiac activity. In some cases, the controller 30 may receive signals that include an electrical indication of an atrial (or other) contraction (e.g. a P-wave of an ECG 16, see FIG. 2). In some cases, the controller 30 may receive electrical signals (e.g. conducted communication signals) that include an indication of atrial (or other) contractions from a remote device such as the SICD 12 (FIG. 1).

In some cases, the LCP 64 may include a first sensor 66 and a second sensor 68. The first sensor 66 may be disposed within the housing 20 and may be operably coupled to the controller 30 via electrical connections 70. The second sensor 68 may be disposed within the housing 20 and may be operably coupled to the controller 30 via electrical connections 72. In some cases, the first sensor 66 may include an accelerometer. In some instances, the second sensor 68 may include a pressure sensor. In some cases, the first sensor 66 may provide a first sensor signal to the controller 30, where the first sensor signal is responsive to an atrial contraction of the patient' heart. In some cases, the second sensor 68 may provide a second sensor signal to the controller 30, where the second sensor signal is responsive to an atrial contraction of the patient's heart.

In some cases, a signal from the first sensor 66 may be weighted with a first weight and a signal from the second sensor 68 may be weighted with a second weight. In some cases, for example, the first weight applied to the first signal and/or the second weight applied to the second signal may be based at least in part on a confidence level in the corresponding signals. In some cases, the weights may be based at least in part on the Signal-To-Noise ratio (SNR) of the corresponding signals. In some cases, the controller 30 may, for example, preferentially rely more on the first signal from the first sensor 66 and less on the second signal from the second sensor 68. In some instances, the controller 30 may preferentially rely more on the second signal from the second sensor 68 and less on the first signal from the first sensor 66.

In some cases, the controller 30 may be configured to determine a ventricle pace time for delivering a ventricle pacing pulse to the ventricle of the patient's heart. In some cases, the controller 30 may determine the ventricle pace time based at least in part on an indication of an atrial contraction event of the patient's heart, and in some cases an indication of metabolic demand on the patient's heart. The indication of an atrial contraction event may be based primarily or exclusively on the received first signal if the indication of metabolic demand is below a metabolic demand threshold and may be based primarily or exclusively on the received second signal if the indication of metabolic demand is above the metabolic demand threshold. In some cases, the indication of metabolic demand may be based at least in part upon the received first sensor signal. In some cases, the indication of metabolic demand may be based at least in part upon the received second sensor signal. In some instances, the indication of metabolic demand may be based at least in part upon the received electrical cardiac signal. The controller 30 may be configured to generate a ventricle pacing pulse at the ventricle pace time.

In an example, either the first sensor 66 or the second sensor 68 may be an accelerometer, and the controller 30 may be configured to determine a posture of the patient based at least in part on an accelerometer signal from the accelerometer, and may determine an indication of metabolic demand based at least in part on the determined posture. In another example, either the first sensor 66 or the second sensor 68 may be an accelerometer, and the controller 30 may be configured to determine an activity level of the patient based at least in part on an accelerometer signal from the accelerometer, and to determine the indication of metabolic demand based at least in part on the determined activity level.

In another example, the first sensor 66 and the second sensor 68 may include an accelerometer and a pressure sensor, and the controller 30 may be configured to attempt to detect an A-wave via a pressure signal from the pressure sensor. The controller 30 may also determine a ventricle pace time based at least in part on: (1) the A-wave when the A-wave is detected; and (2) one or more of a received pressure signal from the pressure sensor and/or a received accelerometer signal from the accelerometer other than the A-wave when the A-wave is not detected. In another example of the first sensor 66 and the second sensor 68 including an accelerometer and a pressure sensor, the controller 30 may be configured to determine a ventricle pace time based at least in part on an LV pressure parameter indicated in a pressure signal of the pressure sensor when the indication of metabolic demand is above the metabolic demand threshold and to determine the ventricle pace time based at least in part on a heart sound indicated in the pressure signal of the pressure sensor and/or in an accelerometer signal of the accelerometer when the indication of metabolic demand is below the metabolic demand threshold.

In another example of the first sensor 66 and the second sensor 68 including an accelerometer and a pressure sensor, the controller 30 may be configured to detect an S2 heart sound via the pressure sensor and/or the accelerometer and detect an A-wave via the pressure sensor. In some cases, the controller 30 may be configured to determine a ventricle pace time to achieve a smaller S2 to A-wave interval when the indication of metabolic demand exceeds a relaxation threshold and to achieve a larger S2 to A-wave interval when the indication of metabolic demand does not exceed the relaxation threshold. In some cases, the controller 30 may be configured to detect an S2 heart sound via the pressure sensor and/or the accelerometer and to detect an S1 heart sound via the pressure sensor and/or the accelerometer. In some instances, the controller 30 may be configured to determine a ventricle pace time to achieve a smaller S2 to S1 interval when the indication of metabolic demand exceeds a relaxation threshold and to determine the ventricle pace time to achieve a larger S2 to S1 interval when the indication of metabolic demand does not exceed the relaxation threshold. The relaxation threshold is set to correspond to when the patient is in a relaxation (versus active) state.

In some cases, either the first sensor 66 or the second sensor 68 may include a pressure sensor, and the controller 30 may be configured to determine a ventricle pace time to achieve a higher change rate in LV pressure over time (dP/dt) when the indication of metabolic demand is above a relaxation threshold, and to determine a ventricle pace time to achieve a lower change rate in LV pressure over time (dP/dt) when the indication of metabolic demand is below the relaxation threshold. In yet another example, the controller 30 may be configured to determine a ventricle pace time to achieve lower passive ventricular filling when the indication of metabolic demand is above a relaxation threshold, and to determine a ventricle pace time to achieve higher passive ventricular filling when the indication of metabolic demand is below a relaxation threshold.

It is contemplated that the above-referenced relaxation threshold may not be a single threshold. For example, in some cases, the relaxation threshold may include hysteresis, where a different relaxation threshold is applied depending on whether the patient is transitioning from a relaxed state to an active state, or from an active state to a relaxed state.

Figure 8:
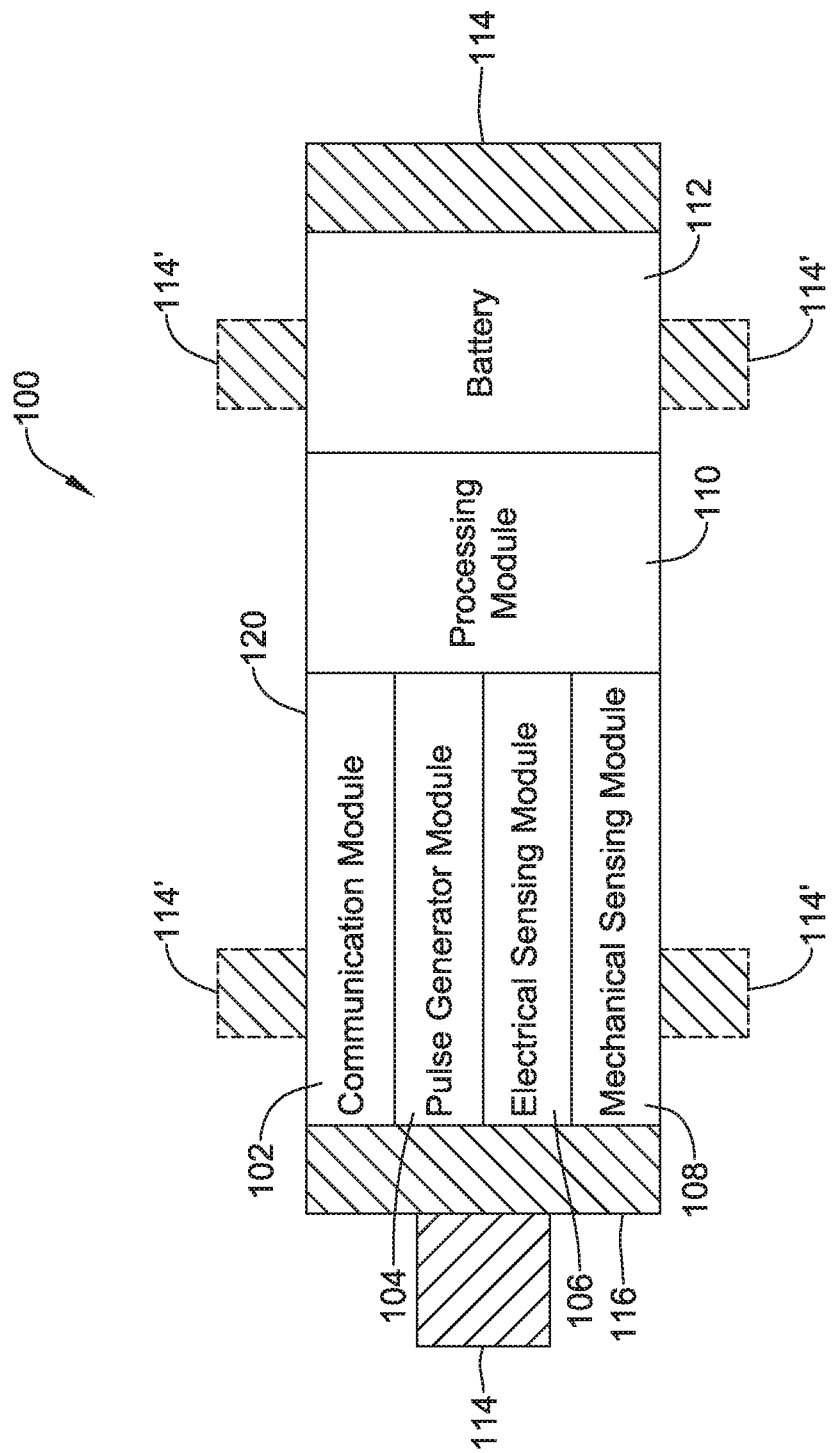
FIG. 8 is a schematic block diagram of an illustrative LCP in accordance with an example of the disclosure.

FIG. 8 depicts another illustrative leadless cardiac pacemaker (LCP) that may be implanted into a patient and may operate to deliver appropriate therapy to the heart, such as to deliver anti-tachycardia pacing (ATP) therapy, cardiac resynchronization therapy (CRT), bradycardia therapy, and/or the like. As can be seen in FIG. 8, the LCP 100 may be a compact device with all components housed within the or directly on a housing 120. In some cases, the LCP 100 may be considered as being an example of one or more of the LCP 14 (FIGS. 1 and 3), the LCP 44 (FIG. 5), the LCP 54 (FIG. 6) and/or the LCP 64 (FIG. 7). In the example shown in FIG. 8, the LCP 100 may include a communication module 102, a pulse generator module 104, an electrical sensing module 106, a mechanical sensing module 108, a processing module 110, a battery 112, and an electrode arrangement 114. The LCP 100 may include more or less modules, depending on the application.

The communication module 102 may be configured to communicate with devices such as sensors, other medical devices such as an SICD, and/or the like, that are located externally to the LCP 100. Such devices may be located either external or internal to the patient's body. Irrespective of the location, external devices (i.e. external to the LCP 100 but not necessarily external to the patient's body) can communicate with the LCP 100 via communication module 102 to accomplish one or more desired functions. For example, the LCP 100 may communicate information, such as sensed electrical signals, data, instructions, messages, R-wave detection markers, etc., to an external medical device through the communication module 102. The external medical device may use the communicated signals, data, instructions, messages, R-wave detection markers, etc., to perform various functions, such as determining occurrences of arrhythmias, delivering electrical stimulation therapy, storing received data, and/or performing any other suitable function. The LCP 100 may additionally receive information such as signals, data, instructions and/or messages from the external medical device through the communication module 102, and the LCP 100 may use the received signals, data, instructions and/or messages to perform various functions, such as determining occurrences of arrhythmias, delivering electrical stimulation therapy, storing received data, and/or performing any other suitable function. The communication module 102 may be configured to use one or more methods for communicating with external devices. For example, the communication module 102 may communicate via radiofrequency (RF) signals, inductive coupling, optical signals, acoustic signals, conducted communication signals, and/or any other signals suitable for communication.

In the example shown in FIG. 8, the pulse generator module 104 may be electrically connected to the electrodes 114. In some examples, the LCP 100 may additionally include electrodes 114'. In such examples, the pulse generator 104 may also be electrically connected to the electrodes 114'. The pulse generator module 104 may be configured to generate electrical stimulation signals. For example, the pulse generator module 104 may generate and deliver electrical stimulation signals by using energy stored in the battery 112 within the LCP 100 and deliver the generated electrical stimulation signals via the electrodes 114 and/or 114'. Alternatively, or additionally, the pulse generator 104 may include one or more capacitors, and the pulse generator 104 may charge the one or more capacitors by drawing energy from the battery 112. The pulse generator 104 may then use the energy of the one or more capacitors to deliver the generated electrical stimulation signals via the electrodes 114 and/or 114'. In at least some examples, the pulse generator 104 of the LCP 100 may include switching circuitry to selectively connect one or more of the electrodes 114 and/or 114' to the pulse generator 104 in order to select which of the electrodes 114/114' (and/or other electrodes) the pulse generator 104 delivers the electrical stimulation therapy. The pulse generator module 104 may generate and deliver electrical stimulation signals with particular features or in particular sequences in order to provide one or multiple of a number of different stimulation therapies. For example, the pulse generator module 104 may be configured to generate electrical stimulation signals to provide electrical stimulation therapy to combat bradycardia, tachycardia, cardiac synchronization, bradycardia arrhythmias, tachycardia arrhythmias, fibrillation arrhythmias, cardiac synchronization arrhythmias and/or to produce any other suitable electrical stimulation therapy. Some more common electrical stimulation therapies include anti-tachycardia pacing (ATP) therapy, cardiac resynchronization therapy (CRT), and cardioversion/defibrillation therapy.

In some examples, the LCP 100 may not include a pulse generator 104. For example, the LCP 100 may be a diagnostic only device. In such examples, the LCP 100 may not deliver electrical stimulation therapy to a patient. Rather, the LCP 100 may collect data about cardiac electrical activity and/or physiological parameters of the patient and communicate such data and/or determinations to one or more other medical devices via the communication module 102.

In some examples, the LCP 100 may include an electrical sensing module 106, and in some cases, a mechanical sensing module 108. The electrical sensing module 106 may be configured to sense the cardiac electrical activity of the heart. For example, the electrical sensing module 106 may be connected to the electrodes 114/114', and the electrical sensing module 106 may be configured to receive cardiac electrical signals conducted through the electrodes 114/114'. The cardiac electrical signals may represent local information from the chamber in which the LCP 100 is implanted. For instance, if the LCP 100 is implanted within a ventricle of the heart (e.g. RV, LV), cardiac electrical signals sensed by the LCP 100 through the electrodes 114/114' may represent ventricular cardiac electrical signals. In some cases, the LCP 100 may be configured to detect cardiac electrical signals from other chambers (e.g. far field), such as the P-wave from the atrium.

The mechanical sensing module 108 may include one or more sensors, such as an accelerometer, a pressure sensor, a heart sound sensor, a blood-oxygen sensor, a chemical sensor, a temperature sensor, a flow sensor and/or any other suitable sensors that are configured to measure one or more mechanical/chemical parameters of the patient. Both the electrical sensing module 106 and the mechanical sensing module 108 may be connected to a processing module 110, which may provide signals representative of the sensed mechanical parameters. Although described with respect to FIG. 8 as separate sensing modules, in some cases, the electrical sensing module 206 and the mechanical sensing module 208 may be combined into a single sensing module, as desired.

The electrodes 114/114' can be secured relative to the housing 120 but exposed to the tissue and/or blood surrounding the LCP 100. In some cases, the electrodes 114 may be generally disposed on either end of the LCP 100 and may be in electrical communication with one or more of the modules 102, 104, 106, 108, and 110. The electrodes 114/114' may be supported by the housing 120, although in some examples, the electrodes 114/114' may be connected to the housing 120 through short connecting wires such that the electrodes 114/114' are not directly secured relative to the housing 120. In examples where the LCP 100 includes one or more electrodes 114', the electrodes 114' may in some cases be disposed on the sides of the LCP 100, which may increase the number of electrodes by which the LCP 100 may sense cardiac electrical activity, deliver electrical stimulation and/or communicate with an external medical device. The electrodes 114/114' can be made up of one or more biocompatible conductive materials such as various metals or alloys that are known to be safe for implantation within a human body. In some instances, the electrodes 114/114' connected to the LCP 100 may have an insulative portion that electrically isolates the electrodes 114/114' from adjacent electrodes, the housing 120, and/or other parts of the LCP 100. In some cases, one or more of the electrodes 114/114' may be provided on a tail (not shown) that extends away from the housing 120.

The processing module 110 can be configured to control the operation of the LCP 100. For example, the processing module 110 may be configured to receive electrical signals from the electrical sensing module 106 and/or the mechanical sensing module 108. Based on the received signals, the processing module 110 may determine, for example, abnormalities in the operation of the heart H. Based on any determined abnormalities, the processing module 110 may control the pulse generator module 104 to generate and deliver electrical stimulation in accordance with one or more therapies to treat the determined abnormalities. The processing module 110 may further receive information from the communication module 102. In some examples, the processing module 110 may use such received information to help determine whether an abnormality is occurring, determine a type of abnormality, and/or to take particular action in response to the information. The processing module 110 may additionally control the communication module 102 to send/receive information to/from other devices.

In some examples, the processing module 110 may include a pre-programmed chip, such as a very-large-scale integration (VLSI) chip and/or an application specific integrated circuit (ASIC). In such embodiments, the chip may be pre-programmed with control logic in order to control the operation of the LCP 100. By using a pre-programmed chip, the processing module 110 may use less power than other programmable circuits (e.g. general purpose programmable microprocessors) while still being able to maintain basic functionality, thereby potentially increasing the battery life of the LCP 100. In other examples, the processing module 110 may include a programmable microprocessor. Such a programmable microprocessor may allow a user to modify the control logic of the LCP 100 even after implantation, thereby allowing for greater flexibility of the LCP 100 than when using a pre-programmed ASIC. In some examples, the processing module 110 may further include a memory, and the processing module 110 may store information on and read information from the memory. In other examples, the LCP 100 may include a separate memory (not shown) that is in communication with the processing module 110, such that the processing module 110 may read and write information to and from the separate memory.

The battery 112 may provide power to the LCP 100 for its operations. In some examples, the battery 112 may be a non-rechargeable lithium-based battery. In other examples, a non-rechargeable battery may be made from other suitable materials, as desired. Because the LCP 100 is an implantable device, access to the LCP 100 may be limited after implantation. Accordingly, it is desirable to have sufficient battery capacity to deliver therapy over a period of treatment such as days, weeks, months, years or even decades. In some instances, the battery 112 may a rechargeable battery, which may help increase the useable lifespan of the LCP 100. In still other examples, the battery 110 may be some other type of power source, as desired.

To implant the LCP 100 inside a patient's body, an operator (e.g., a physician, clinician, etc.), may fix the LCP 100 to the cardiac tissue of the patient's heart. To facilitate fixation, the LCP 100 may include one or more anchors 116. The anchor 116 may include any one of a number of fixation or anchoring mechanisms. For example, the anchor 116 may include one or more pins, staples, threads, screws, helix, tines, and/or the like. In some examples, although not shown, the anchor 116 may include threads on its external surface that may run along at least a partial length of the anchor 116. The threads may provide friction between the cardiac tissue and the anchor to help fix the anchor 116 within the cardiac tissue. In other examples, the anchor 116 may include other structures such as barbs, spikes, or the like to facilitate engagement with the surrounding cardiac tissue.

Figure 9:
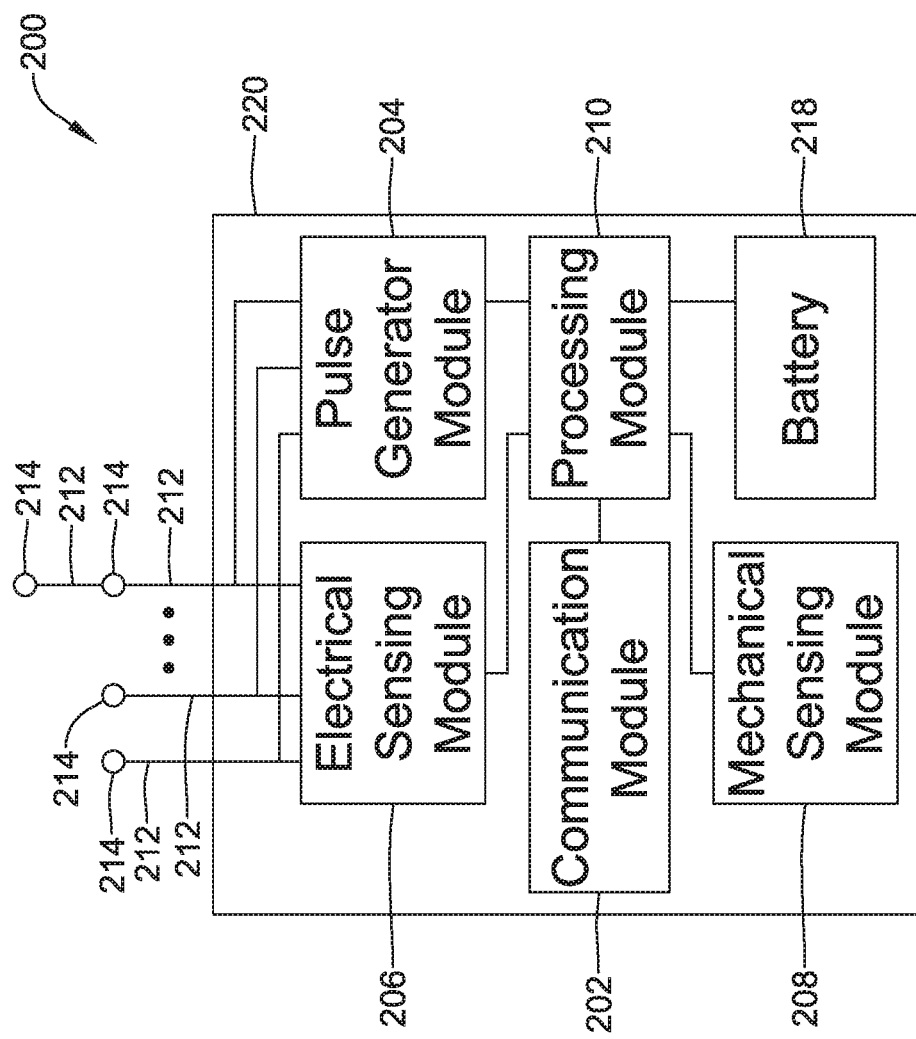
FIG. 9 is a schematic block diagram of another illustrative medical device that may be used in conjunction with the LCP of FIG. 8.

FIG. 9 depicts an example of another medical device (MD) 200, which may be used in conjunction with the LCP 100 (FIG. 8) in order to detect and/or treat cardiac abnormalities. In some cases, the MD 200 may be considered as an example of the SICD 12 (FIG. 1). In the example shown, the MD 200 may include a communication module 202, a pulse generator module 204, an electrical sensing module 206, a mechanical sensing module 208, a processing module 210, and a battery 218. Each of these modules may be similar to the modules 102, 104, 106, 108, and 110 of LCP 100. Additionally, the battery 218 may be similar to the battery 112 of the LCP 100. In some examples, however, the MD 200 may have a larger volume within the housing 220. In such examples, the MD 200 may include a larger battery and/or a larger processing module 210 capable of handling more complex operations than the processing module 110 of the LCP 100.

While it is contemplated that the MD 200 may be another leadless device such as shown in FIG. 8, in some instances the MD 200 may include leads such as leads 212. The leads 212 may include electrical wires that conduct electrical signals between the electrodes 214 and one or more modules located within the housing 220. In some cases, the leads 212 may be connected to and extend away from the housing 220 of the MD 200. In some examples, the leads 212 are implanted on, within, or adjacent to a heart of a patient. The leads 212 may contain one or more electrodes 214 positioned at various locations on the leads 212, and in some cases at various distances from the housing 220. Some leads 212 may only include a single electrode 214, while other leads 212 may include multiple electrodes 214. Generally, the electrodes 214 are positioned on the leads 212 such that when the leads 212 are implanted within the patient, one or more of the electrodes 214 are positioned to perform a desired function. In some cases, the one or more of the electrodes 214 may be in contact with the patient's cardiac tissue. In some cases, the one or more of the electrodes 214 may be positioned subcutaneously and outside of the patient's heart. In some cases, the electrodes 214 may conduct intrinsically generated electrical signals to the leads 212, e.g. signals representative of intrinsic cardiac electrical activity. The leads 212 may, in turn, conduct the received electrical signals to one or more of the modules 202, 204, 206, and 208 of the MD 200. In some cases, the MD 200 may generate electrical stimulation signals, and the leads 212 may conduct the generated electrical stimulation signals to the electrodes 214. The electrodes 214 may then conduct the electrical signals and delivery the signals to the patient's heart (either directly or indirectly).

The mechanical sensing module 208, as with the mechanical sensing module 108, may contain or be electrically connected to one or more sensors, such as accelerometers, acoustic sensors, blood pressure sensors, heart sound sensors, blood-oxygen sensors, and/or other sensors which are configured to measure one or more mechanical/chemical parameters of the heart and/or patient. In some examples, one or more of the sensors may be located on the leads 212, but this is not required. In some examples, one or more of the sensors may be located in the housing 220.

While not required, in some examples, the MD 200 may be an implantable medical device. In such examples, the housing 220 of the MD 200 may be implanted in, for example, a transthoracic region of the patient. The housing 220 may generally include any of a number of known materials that are safe for implantation in a human body and may, when implanted, hermetically seal the various components of the MD 200 from fluids and tissues of the patient's body.

In some cases, the MD 200 may be an implantable cardiac pacemaker (ICP). In this example, the MD 200 may have one or more leads, for example the leads 212, which are implanted on or within the patient's heart. The one or more leads 212 may include one or more electrodes 214 that are in contact with cardiac tissue and/or blood of the patient's heart. The MD 200 may be configured to sense intrinsically generated cardiac electrical signals and determine, for example, one or more cardiac arrhythmias based on analysis of the sensed signals. The MD 200 may be configured to deliver CRT, ATP therapy, bradycardia therapy, and/or other therapy types via the leads 212 implanted within the heart.

In some examples, the MD 200 may additionally be configured provide defibrillation therapy.

In some instances, the MD 200 may be an implantable cardioverter-defibrillator (ICD). In such examples, the MD 200 may include one or more leads implanted within a patient's heart. The MD 200 may also be configured to sense cardiac electrical signals, determine occurrences of tachyarrhythmias based on the sensed signals, and may be configured to deliver defibrillation therapy in response to determining an occurrence of a tachyarrhythmia. In other examples, the MD 200 may be a subcutaneous implantable cardioverter-defibrillator (S-ICD). In examples where the MD 200 is an S-ICD, one of the leads 212 may be a subcutaneously implanted lead. In at least some examples where the MD 200 is an S-ICD, the MD 200 may include only a single lead which is implanted subcutaneously, but this is not required. In some instances, the lead(s) may have one or more electrodes that are placed subcutaneously and outside of the chest cavity. In other examples, the lead(s) may have one or more electrodes that are placed inside of the chest cavity, such as just interior of the sternum.

In some examples, the MD 200 may not be an implantable medical device. Rather, the MD 200 may be a device external to the patient's body, and may include skin-electrodes that are placed on a patient's body. In such examples, the MD 200 may be able to sense surface electrical signals (e.g. cardiac electrical signals that are generated by the heart or electrical signals generated by a device implanted within a patient's body and conducted through the body to the skin). In such examples, the MD 200 may be configured to deliver various types of electrical stimulation therapy, including, for example, defibrillation therapy.

Figure 10:
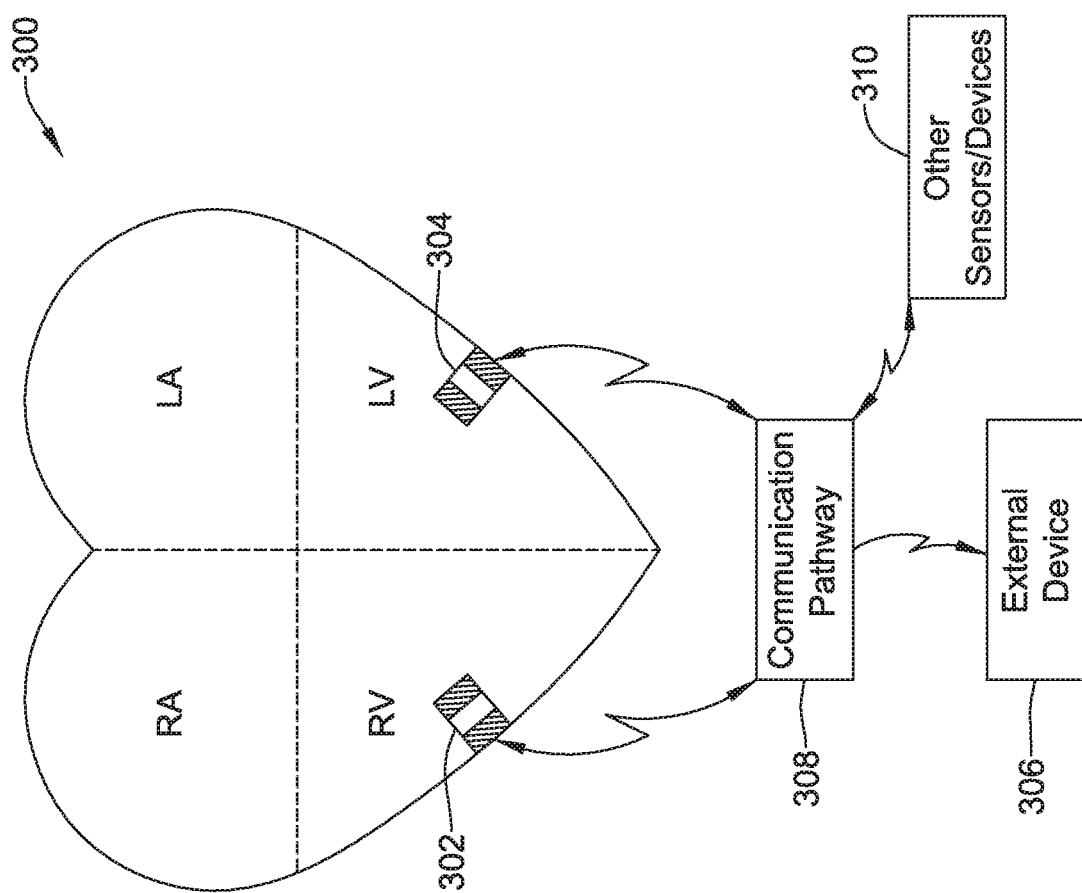
FIG. 10 is a schematic diagram of an exemplary medical system that includes multiple LCPs and/or other devices in communication with one another.

FIG. 10 illustrates an example of a medical device system and a communication pathway through which multiple medical devices 302, 304, 306, and/or 310 may communicate. In the example shown, the medical device system 300 may include LCPs 302 and 304, external medical device 306, and other sensors/devices 310. The external device 306 may be any of the devices described previously with respect to the MD 200. Other sensors/devices 310 may also be any of the devices described previously with respect to the MD 200. In some instances, other sensors/devices 310 may include a sensor, such as an accelerometer, an acoustic sensor, a blood pressure sensor, or the like. In some cases, other sensors/devices 310 may include an external programmer device that may be used to program one or more devices of the system 300.

Various devices of the system 300 may communicate via communication pathway 308. For example, the LCPs 302 and/or 304 may sense intrinsic cardiac electrical signals and may communicate such signals to one or more other devices 302/304, 306, and 310 of the system 300 via communication pathway 308. In one example, one or more of the devices 302/304 may receive such signals and, based on the received signals, determine an occurrence of an arrhythmia. In some cases, the device or devices 302/304 may communicate such determinations to one or more other devices 306 and 310 of the system 300. In some cases, one or more of the devices 302/304, 306, and 310 of the system 300 may take action based on the communicated determination of an arrhythmia, such as by delivering a suitable electrical stimulation to the heart of the patient. It is contemplated that the communication pathway 308 may communicate using RF signals, inductive coupling, optical signals, acoustic signals, or any other signals suitable for communication. Additionally, in at least some examples, device communication pathway 308 may include multiple signal types. For instance, other sensors/device 310 may communicate with the external device 306 using a first signal type (e.g. RF communication) but communicate with the LCPs 302/304 using a second signal type (e.g. conducted communication). Further, in some examples, communication between devices may be limited. For instance, as described above, in some examples, the LCPs 302/304 may communicate with the external device 306 only through other sensors/devices 310, where the LCPs 302/304 send signals to other sensors/devices 310, and other sensors/devices 310 relay the received signals to the external device 306.

In some cases, the communication pathway 308 may include conducted communication. Accordingly, devices of the system 300 may have components that allow for such conducted communication. For instance, the devices of system 300 may be configured to transmit conducted communication signals (e.g. current and/or voltage pulses) into the patient's body via one or more electrodes of a transmitting device, and may receive the conducted communication signals (e.g. pulses) via one or more electrodes of a receiving device. The patient's body may "conduct" the conducted communication signals (e.g. pulses) from the one or more electrodes of the transmitting device to the electrodes of the receiving device in the system 300. In such examples, the delivered conducted communication signals (e.g. pulses) may differ from pacing or other therapy signals. For example, the devices of the system 300 may deliver electrical communication pulses at an amplitude/pulse width that is sub-threshold to the heart. Although, in some cases, the amplitude/pulse width of the delivered electrical communication pulses may be above the capture threshold of the heart, but may be delivered during a blanking period of the heart and/or may be incorporated in or modulated onto a pacing pulse, if desired.

Delivered electrical communication pulses may be modulated in any suitable manner to encode communicated information. In some cases, the communication pulses may be pulse width modulated or amplitude modulated. Alternatively, or in addition, the time between pulses may be modulated to encode desired information. In some cases, conducted communication pulses may be voltage pulses, current pulses, biphasic voltage pulses, biphasic current pulses, or any other suitable electrical pulse as desired.

Figure 11:
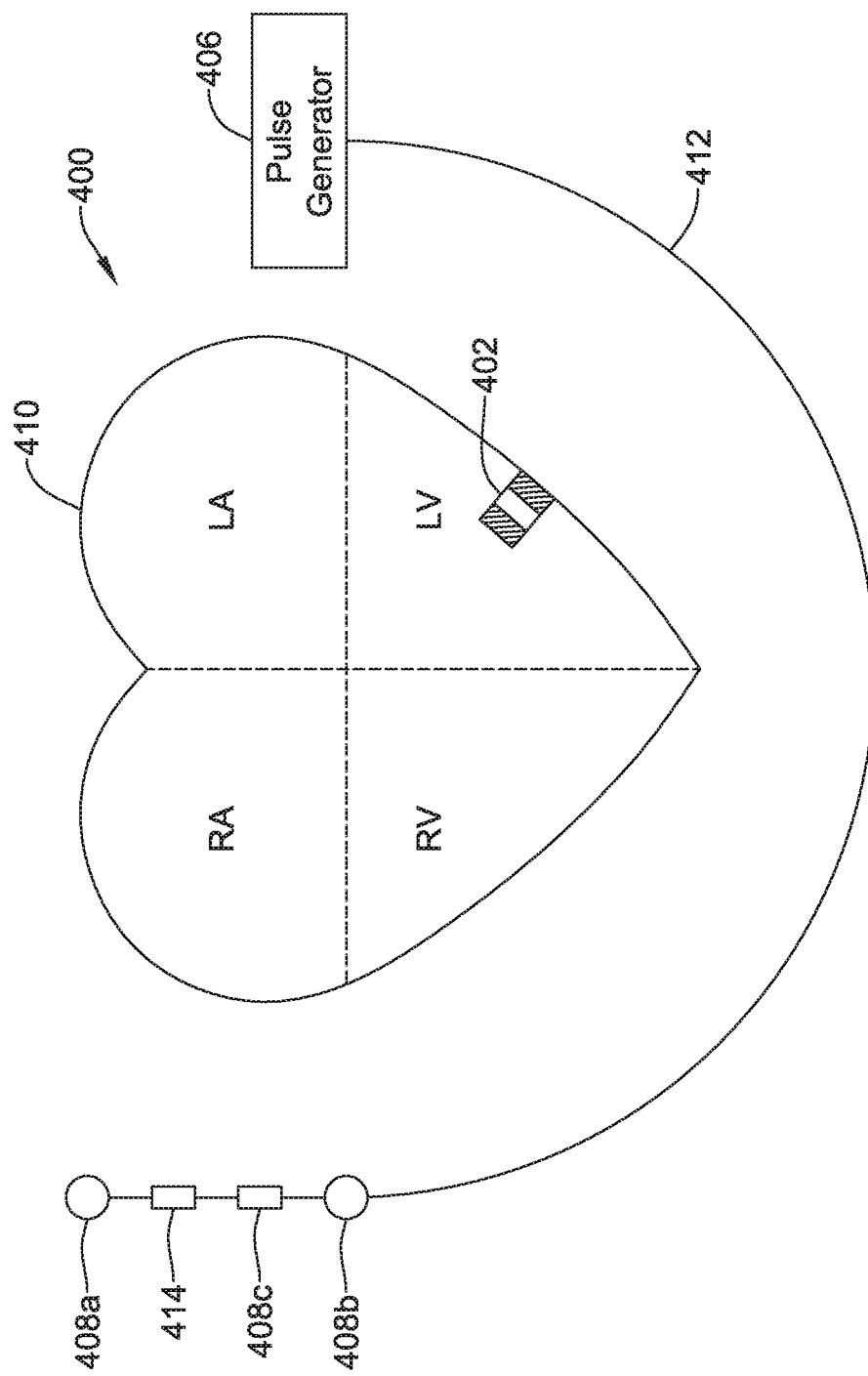
FIG. 11 is a schematic diagram of a system including an LCP and another medical device, in accordance with an example of the disclosure.

FIG. 11 shows an illustrative medical device systems. In FIG. 11, an LCP 402 is shown fixed to the interior of the left ventricle of the heart 410, and a pulse generator 406 is shown coupled to a lead 412 having one or more electrodes 408a-408c. In some cases, the pulse generator 406 may be part of a subcutaneous implantable cardioverter-defibrillator (S-ICD), and the one or more electrodes 408a-408c may be positioned subcutaneously. In some cases, the one or more electrodes 408a-408c may be placed inside of the chest cavity but outside of the heart, such as just interior of the sternum.

In some cases, the LCP 402 may communicate with the subcutaneous implantable cardioverter-defibrillator (S-ICD). In some cases, the lead 412 may include an accelerometer 414 that may, for example, be configured to sense vibrations that may be indicative of heart sounds.

In some cases, the LCP 402 may be in the right ventricle, right atrium, left ventricle or left atrium of the heart, as desired. In some cases, more than one LCP 402 may be implanted. For example, one LCP may be implanted in the right ventricle and another may be implanted in the right atrium. In another example, one LCP may be implanted in the right ventricle and another may be implanted in the left ventricle. In yet another example, one LCP may be implanted in each of the chambers of the heart.

When an LCP is placed in, for example, the left ventricle, and no LCP is placed in the left atrium, techniques of the present disclosure may be used to help determine an atrial contraction timing fiducial for the left atrium. This atrial contraction timing fiducial may then be used to determine a proper time to pace the left ventricle via the LCP, such as an AV delay after the atrial contraction timing fiducial.

Figure 12:
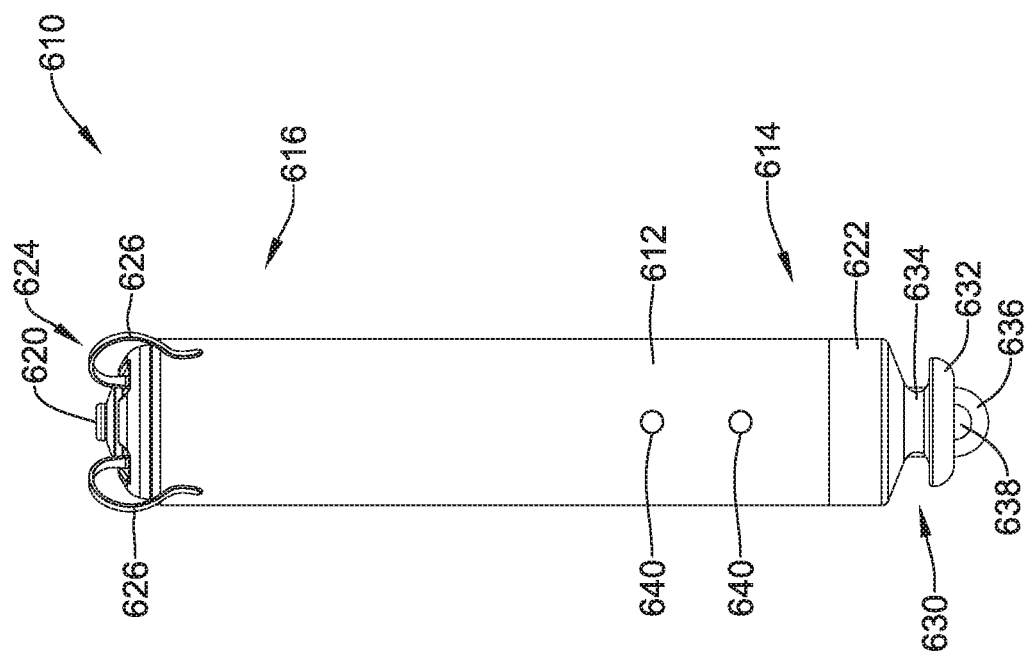
FIG. 12 is a side view of an illustrative implantable leadless cardiac device.

FIG. 12 is a side view of an illustrative implantable leadless cardiac pacemaker (LCP) 610. The LCP 610 may be similar in form and function to the LCP 100 described above. The LCP 610 may include any of the modules and/or structural features described above with respect to the LCP 100 described above. The LCP 610 may include a shell or housing 612 having a proximal end 614 and a distal end 616. The illustrative LCP 610 includes a first electrode 620 secured relative to the housing 612 and positioned adjacent to the distal end 616 of the housing 612 and a second electrode 622 secured relative to the housing 612 and positioned adjacent to the proximal end 614 of the housing 612. In some cases, the housing 612 may include a conductive material and may be insulated along a portion of its length. A section along the proximal end 614 may be free of insulation so as to define the second electrode 622. The electrodes 620, 622 may be sensing and/or pacing electrodes to provide electro-therapy and/or sensing capabilities. The first electrode 620 may be capable of being positioned against or may otherwise contact the cardiac tissue of the heart while the second electrode 622 may be spaced away from the first electrode 620. The first and/or second electrodes 620, 622 may be exposed to the environment outside the housing 612 (e.g. to blood and/or tissue).

In some cases, the LCP 610 may include a pulse generator (e.g., electrical circuitry) and a power source (e.g., a battery) within the housing 612 to provide electrical signals to the electrodes 620, 622 to control the pacing/sensing electrodes 620, 622. While not explicitly shown, the LCP 610 may also include, a communications module, an electrical sensing module, a mechanical sensing module, and/or a processing module, and the associated circuitry, similar in form and function to the modules 102, 106, 108, 110 described above. The various modules and electrical circuitry may be disposed within the housing 612. Electrical communication between the pulse generator and the electrodes 620, 622 may provide electrical stimulation to heart tissue and/or sense a physiological condition.

In the example shown, the LCP 610 includes a fixation mechanism 624 proximate the distal end 616 of the housing 612. The fixation mechanism 624 is configured to attach the LCP 610 to a wall of the heart H, or otherwise anchor the LCP 610 to the anatomy of the patient. In some instances, the fixation mechanism 624 may include one or more, or a plurality of hooks or tines 626 anchored into the cardiac tissue of the heart H to attach the LCP 610 to a tissue wall. In other instances, the fixation mechanism 624 may include one or more, or a plurality of passive tines, configured to entangle with trabeculae within the chamber of the heart H and/or a helical fixation anchor configured to be screwed into a tissue wall to anchor the LCP 610 to the heart H. These are just examples.

The LCP 610 may further include a docking member 630 proximate the proximal end 614 of the housing 612. The docking member 630 may be configured to facilitate delivery and/or retrieval of the LCP 610. For example, the docking member 630 may extend from the proximal end 614 of the housing 612 along a longitudinal axis of the housing 612. The docking member 630 may include a head portion 632 and a neck portion 634 extending between the housing 612 and the head portion 632. The head portion 632 may be an enlarged portion relative to the neck portion 634. For example, the head portion 632 may have a radial dimension from the longitudinal axis of the LCP 610 that is greater than a radial dimension of the neck portion 634 from the longitudinal axis of the LCP 610. In some cases, the docking member 630 may further include a tether retention structure 636 extending from or recessed within the head portion 632. The tether retention structure 636 may define an opening 638 configured to receive a tether or other anchoring mechanism therethrough. While the retention structure 636 is shown as having a generally "U-shaped" configuration, the retention structure 636 may take any shape that provides an enclosed perimeter surrounding the opening 638 such that a tether may be securably and releasably passed (e.g. looped) through the opening 638. In some cases, the retention structure 636 may extend though the head portion 632, along the neck portion 634, and to or into the proximal end 614 of the housing 612. The docking member 630 may be configured to facilitate delivery of the LCP 610 to the intracardiac site and/or retrieval of the LCP 610 from the intracardiac site. While this describes one example docking member 630, it is contemplated that the docking member 630, when provided, can have any suitable configuration.

It is contemplated that the LCP 610 may include one or more pressure sensors 640 coupled to or formed within the housing 612 such that the pressure sensor(s) is exposed to the environment outside the housing 612 to measure blood pressure within the heart. For example, if the LCP 610 is placed in the left ventricle, the pressure sensor(s) 640 may measure the pressure within the left ventricle. If the LCP 610 is placed in another portion of the heart (such as one of the atriums or the right ventricle), the pressures sensor(s) may measure the pressure within that portion of the heart. The pressure sensor(s) 640 may include a MEMS device, such as a MEMS device with a pressure diaphragm and piezoresistors on the diaphragm, a piezoelectric sensor, a capacitor-Micro-machined Ultrasonic Transducer (cMUT), a condenser, a micro-monometer, or any other suitable sensor adapted for measuring cardiac pressure. The pressures sensor(s) 640 may be part of a mechanical sensing module described herein. It is contemplated that the pressure measurements obtained from the pressures sensor(s) 640 may be used to generate a pressure curve over cardiac cycles. The pressure readings may be taken in combination with impedance measurements (e.g. the impedance between electrodes 620 and 622) to generate a pressure-impedance loop for one or more cardiac cycles as will be described in more detail below. The impedance may be a surrogate for chamber volume, and thus the pressure-impedance loop may be representative for a pressure-volume loop for the heart H.

In some embodiments, the LCP 610 may be configured to measure impedance between the electrodes 620, 622. More generally, the impedance may be measured between other electrode pairs, such as the additional electrodes 114' described above. In some cases, the impedance may be measure between two spaced LCP's, such as two LCP's implanted within the same chamber (e.g. LV) of the heart H, or two LCP's implanted in different chambers of the heart H (e.g. RV and LV). The processing module of the LCP 610 and/or external support devices may derive a measure of cardiac volume from intracardiac impedance measurements made between the electrodes 620, 622 (or other electrodes). Primarily due to the difference in the resistivity of blood and the resistivity of the cardiac tissue of the heart H, the impedance measurement may vary during a cardiac cycle as the volume of blood (and thus the volume of the chamber) surrounding the LCP changes. In some cases, the measure of cardiac volume may be a relative measure, rather than an actual measure. In some cases, the intracardiac impedance may be correlated to an actual measure of cardiac volume via a calibration process, sometimes performed during implantation of the LCP(s). During the calibration process, the actual cardiac volume may be determined using fluoroscopy or the like, and the measured impedance may be correlated to the actual cardiac volume.

In some cases, the LCP 610 may be provided with energy delivery circuitry operatively coupled to the first electrode 620 and the second electrode 622 for causing a current to flow between the first electrode 620 and the second electrode 622 in order to determine the impedance between the two electrodes 620, 622 (or other electrode pair). It is contemplated that the energy delivery circuitry may also be configured to deliver pacing pulses via the first and/or second electrodes 620, 622. The LCP 610 may further include detection circuitry operatively coupled to the first electrode 620 and the second electrode 622 for detecting an electrical signal received between the first electrode 620 and the second electrode 622. In some instances, the detection circuitry may be configured to detect cardiac signals received between the first electrode 620 and the second electrode 622.

When the energy delivery circuitry delivers a current between the first electrode 620 and the second electrode 622, the detection circuitry may measure a resulting voltage between the first electrode 620 and the second electrode 622 (or between a third and fourth electrode separate from the first electrode 620 and the second electrode 622) to determine the impedance. When the energy delivery circuitry delivers a voltage between the first electrode 620 and the second electrode 622, the detection circuitry may measure a resulting current between the first electrode 620 and the second electrode 622 (or between a third and fourth electrode separate from the first electrode 620 and the second electrode 622) to determine the impedance.

In some instances, the impedance may be measured between electrodes on different devices and/or in different heart chambers. For example, impedance may be measured between a first electrode in the left ventricle and a second electrode in the right ventricle. In another example, impedance may be measured between a first electrode of a first LCP in the left ventricle and a second LCP in the left ventricle. In yet another example, impedance may be measured from an injected current. For example, a medical device (such as, but not limited to an SICD such as the SICD 12 of FIG. 1), may inject a known current into the heart and the LCP implanted in the heart H may measure a voltage resulting from the injected current to determine the impedance. These are just some examples.

Figure 13:
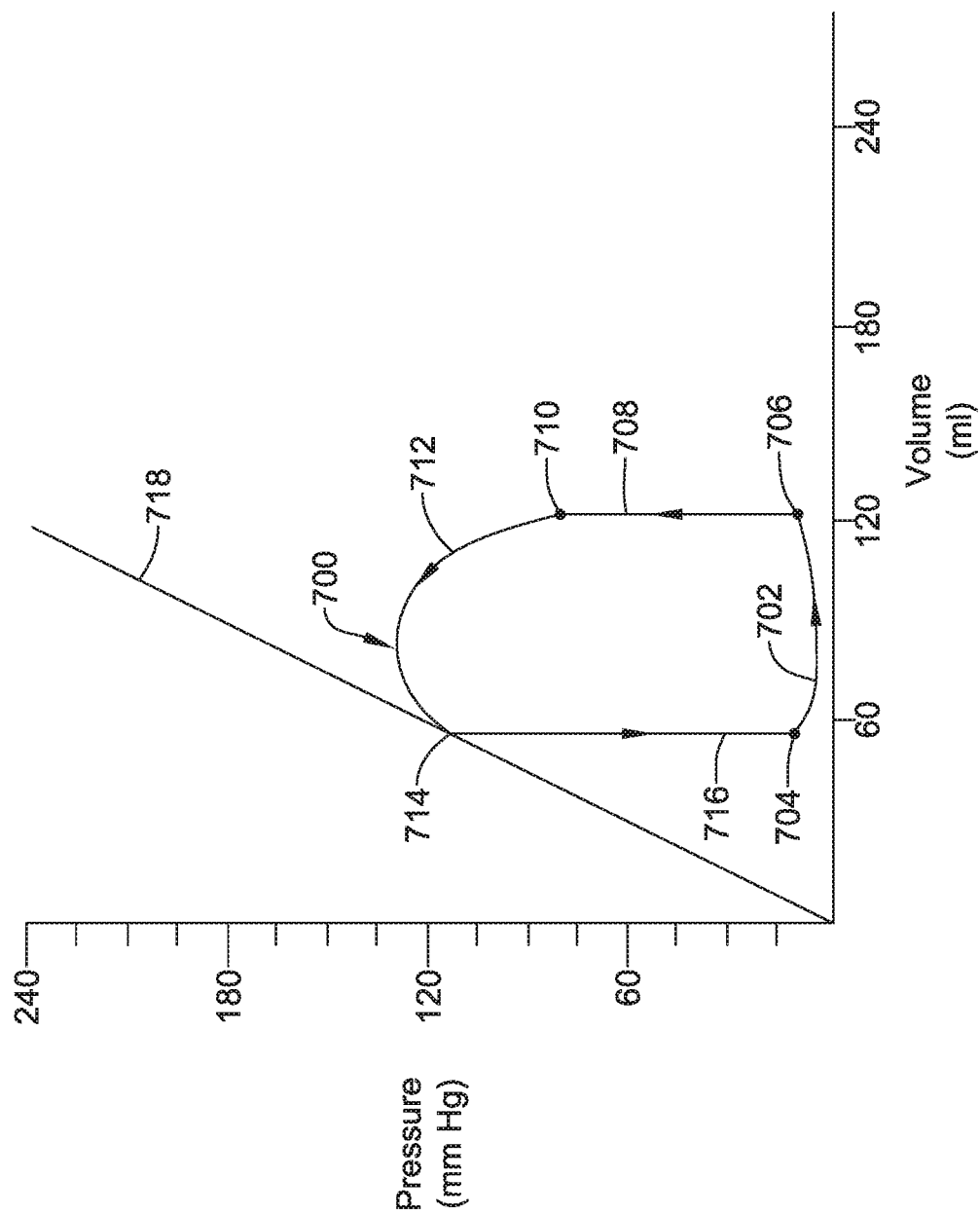
FIG. 13 is an illustrative pressure-volume loop for a ventricle of a human heart.

FIG. 13 illustrates a method of representing pressure and volume parameters of the heart in a pressure-volume (PV) loop. PV loops can be used to determine performance characteristics of the heart H. An illustrative PV loop 700 shows a normal PV characteristics for the left ventricle of the heart. The PV loop 700 moves in a counter-clockwise direction. The mitral valve opens at 704 and ventricular filling occurs along 702. Ventricular filling 702 ends at the point 706 with closure of the mitral valve. The closure of the mitral valve causes the S1 heart sound at 706. The point 706 represents the end diastolic volume (EDV) or the volume of blood in the heart at the end of its dilatation phase. The ventricle contracts at 706. Before the aortic valve opens at 710, an isovolumetric contraction phase occurs along 708 where the ventricle pressure rapidly increases but the ventricle volume does not significantly change. The ejection phase 712 lasts from point 710 until the aortic valve closes at the point 714. The closure of the aortic valve at point 714 generates the S2 heart sound, and also marks the end systolic volume (ESV), or the volume of blood in the heart at the end of its contraction phase. The isovolumetric relaxation phase 716 begins at the point 714 and continues until the mitral valve opens at point 704 and the cardiac cycle repeats. In some cases, the PV loop 700 can be approximated if the points 704, 706, 710, and 714 (the four "corners" of the PV loop) are known, for example.

The contractility index represents the capacity of the muscle to become shorter in response to a suitable stimulus. A measure of the contractility index can be estimated by calculating the slope of the end systolic pressure-volume line (shown as 718). A measure of the stroke work can be estimated by the area of the PV loop 700. A measure of the stroke volume can be estimated by the EDV minus the ESV, and represents the amount of blood ejected from the heart with each heartbeat. A measure of the ejection fraction (the proportion of the volume of blood in the ventricles at the end of diastole that is ejected during systole) can be estimated by the stroke volume divided by the EDV. These are only illustrative, and it is contemplated that other parameters may also be extracted or derived from the PV loop 700.

Figure 14:
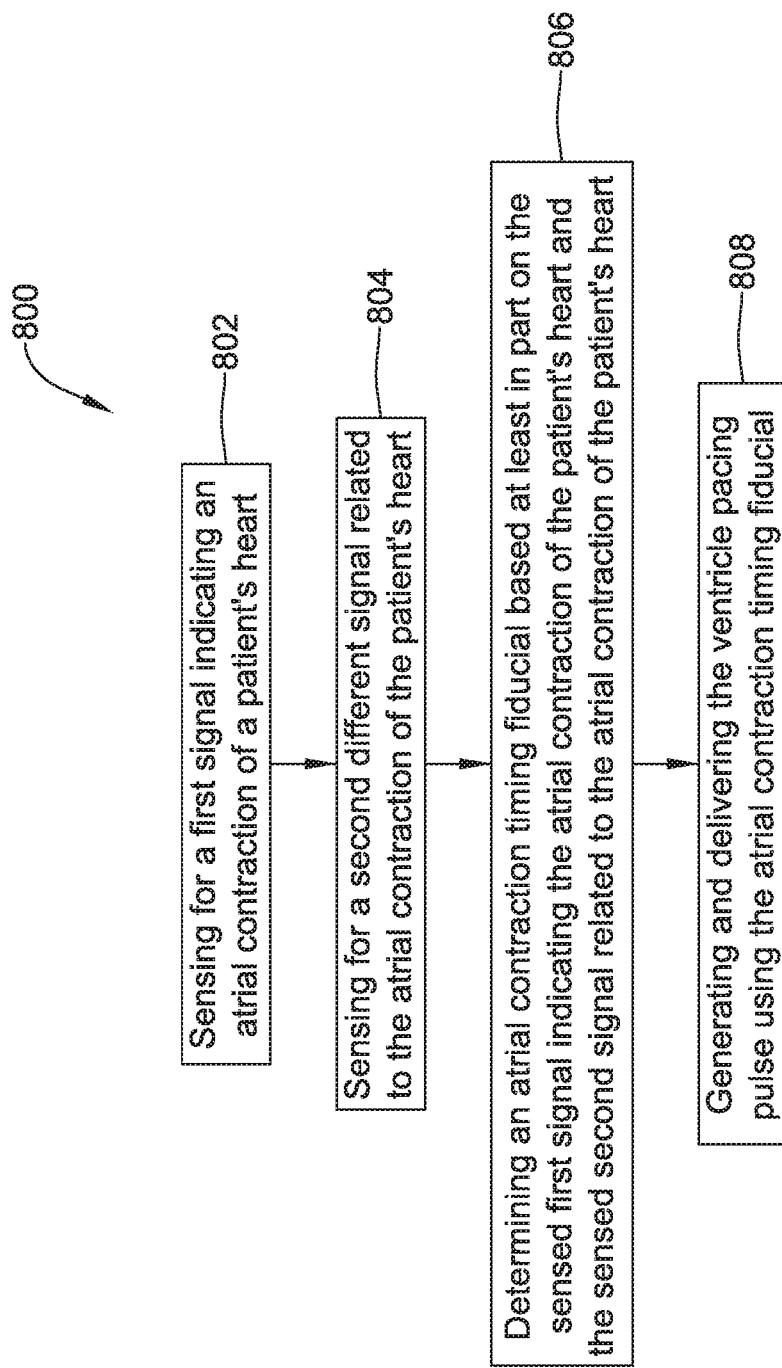
FIG. 14 is a flow diagram of an illustrative method for generating a ventricle pacing pulse.

FIG. 14 is a flow diagram showing an illustrative method 800 of generating a ventricular pulse using an LCP that is disposed with the left ventricle LV. In some cases, as indicated at block 802, a first signal indicating an atrial contraction of a patient's heart may be sensed. A second different signal related to the atrial contraction of the patient's heart may also be sensed as indicated at block 804. In some instances, the first signal and/or the second signal may be generated via a pressure sensor within the LCP. In some cases, the second signal related to the atrial contraction of the patient's heart may include an indication of a ventricular contraction of the patient's heart following the atrial contraction of the patient's heart. The controller may, as indicated at block 806, determine an atrial contraction timing fiducial based at least in part on the sensed first signal indicating the atrial contraction of the patient's heart and the sensed second signal related to the atrial contraction of the patient's heart. A ventricle pacing pulse may be generated and delivered using the atrial contraction timing fiducial, as indicated at block 808.

Figure 15:
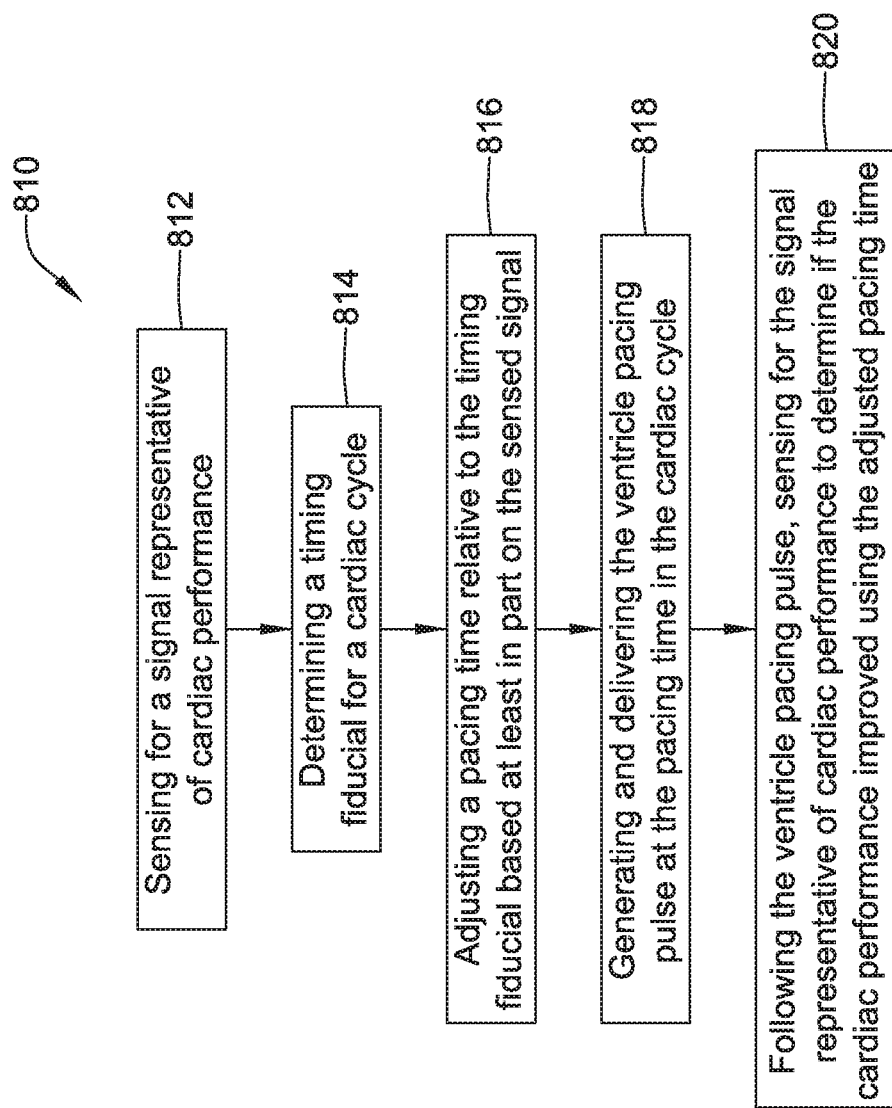
FIG. 15 is a flow diagram of an illustrative method for generating a ventricle pacing pulse.

FIG. 15 is a flow diagram showing another illustrative method 810 of generating and delivering a ventricular pulse using an LCP that is disposed with the left ventricle LV. As generally indicated at block 812, a signal representative of cardiac performance may be sensed. A timing fiducial may be determined for a cardiac cycle, as indicated at block 814. A pacing time may be adjusted relative to the timing fiducial based at least in part on the sensed signal representative of cardiac performance as indicated at block 816. As indicated at block 818, a ventricle pacing pulse may be generated and delivered at the pacing time in the cardiac cycle. Following the ventricle pacing pulse, the method 810 may include sensing for the signal representative of cardiac performance to determine if the cardiac performance improved using the adjusted pacing time, as indicated at block 820.

Figure 16:
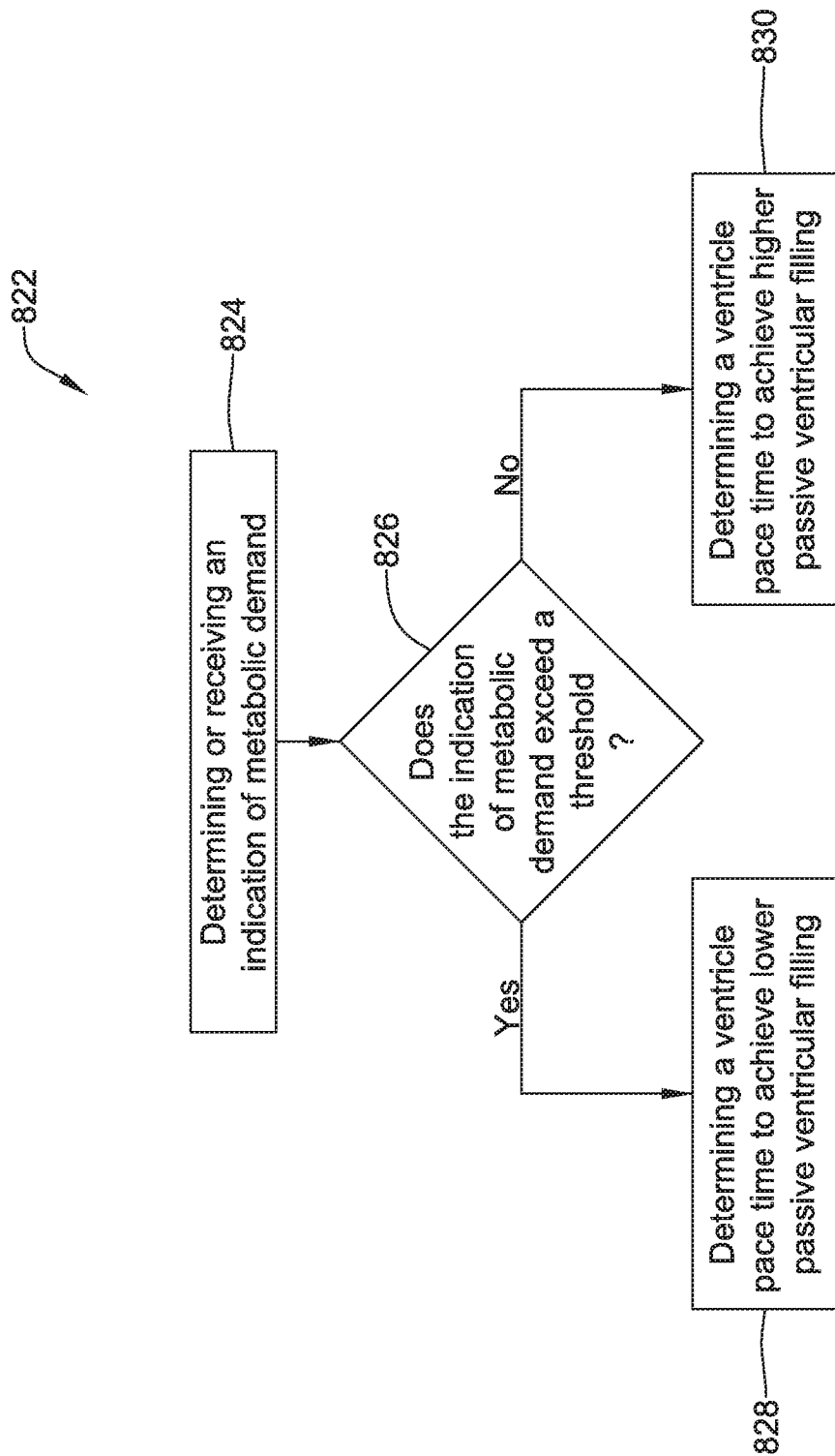
FIG. 16 is a flow diagram of an illustrative method for determining a ventricle pace time.

FIG. 16 is a flow diagram showing an illustrative method 822 of determining a ventricular pace time using an LCP that is disposed with the left ventricle LV. As seen at block 824, an indication of metabolic demand may be determined or received. At decision block 826, a determination is made as to whether the indication of metabolic demand exceeds a threshold. If yes, control passes to block 828 and a ventricle pace time may be determined to achieve lower passive ventricular filling. If not, control passes to block 830 and the ventricle pace time may be determined to achieve higher passive ventricular filling. In some cases, a measure of the passive ventricular filling is based, at least in part on, a pressure signal from a pressure sensor within the LCP.

Those skilled in the art will recognize that the present disclosure may be manifested in a variety of forms other than the specific examples described and contemplated herein. For instance, as described herein, various examples include one or more modules described as performing various functions. However, other examples may include additional modules that split the described functions up over more modules than that described herein. Additionally, other examples may consolidate the described functions into fewer modules. Accordingly, departure in form and detail may be made without departing from the scope and spirit of the present disclosure as described in the appended claims.

What is claimed is:

1. A leadless cardiac pacemaker (LCP) configured to sense cardiac activity and to pace a patient's heart, the LCP disposable within a ventricle of the patient's heart, the LCP comprising:
    a housing;
    a first electrode secured relative to the housing;
    a second electrode secured relative to the housing, the second electrode spaced from the first electrode;
    a controller disposed within the housing and operably coupled to the first electrode and the second electrode such that the controller is capable of receiving an electrical cardiac signal from the patient's heart via the first electrode and the second electrode;
    a first sensor disposed relative to the housing and operably coupled to the controller, the controller configured to receive a first sensor signal from the first sensor, wherein the first sensor comprises an accelerometer and the first sensor signal is responsive to an atrial contraction of the patient's heart;
    a second sensor disposed relative to the housing and operably coupled to the controller, the controller configured to receive a second sensor signal from the second sensor, wherein the second sensor comprises a pressure sensor and the second sensor signal is responsive to an atrial contraction of the patient's heart;
    the controller configured to determine a ventricle pace time for delivering a ventricle pacing pulse to the ventricle of the patient's heart, the controller determining the ventricle pace time based at least in part on an indication of an atrial contraction event of the patient's heart and an indication of metabolic demand on the patient's heart, wherein the indication of an atrial contraction event is based primarily or exclusively on the received first signal if the indication of metabolic demand is below a metabolic demand threshold and is based primarily or exclusively on the received second signal if the indication of metabolic demand is above the metabolic demand threshold; and
    the controller is configured to generate and deliver a ventricle pacing pulse at the ventricle pace time.

2. The LCP of claim 1, wherein the indication of metabolic demand is based at least in part upon the received first sensor signal.

3. The LCP of claim 1, wherein the indication of metabolic demand is based at least in part upon the received second sensor signal.

4. The LCP of claim 1, wherein the indication of metabolic demand is based at least in part upon the received electrical cardiac signal.

5. The LCP of claim 1, wherein the controller is configured to:
    determine a posture of the patient based at least in part on an accelerometer signal from the accelerometer; and
    determine the indication of metabolic demand based at least in part on the determined posture.

6. The LCP of claim 1, wherein the controller is configured to:
    determine an activity level of the patient based at least in part on an accelerometer signal from the accelerometer; and
    determine the indication of metabolic demand based at least in part on the determined activity level.

7. The LCP of claim 1, wherein the controller is configured to:
    attempt to detect an A-wave via a pressure signal from the pressure sensor;
    determine the ventricle pace time based at least in part on the A-wave when the A-wave is detected; and
    determine the ventricle pace time based at least in part on one or more of a received pressure signal from the pressure sensor and/or a received accelerometer signal from the accelerometer other than the A-wave when the A-wave is not detected.

8. The LCP of claim 1, wherein the controller is configured to:
    determine the ventricle pace time based at least in part on an LV pressure parameter indicated in a pressure signal of the pressure sensor when the indication of metabolic demand is above the metabolic demand threshold; and
    determine the ventricle pace time based at least in part on a heart sound indicated in the pressure signal of the pressure sensor and/or in an accelerometer signal of the accelerometer when the indication of metabolic demand is below the metabolic demand threshold.

9. The LCP of claim 1, wherein the controller is configured to:
    determine the ventricle pace time to achieve a higher change rate in LV pressure over time (dP/dt) when the indication of metabolic demand is above a relaxation threshold; and
    determine the ventricle pace time to achieve a lower change rate in LV pressure over time (dP/dt) when the indication of metabolic demand is below the relaxation threshold.

10. The LCP of claim 1, wherein the controller is configured to:
    determine the ventricle pace time to achieve lower passive ventricular filling when the indication of metabolic demand is above a relaxation threshold; and
    determine the ventricle pace time to achieve higher passive ventricular filling when the indication of metabolic demand is below a relaxation threshold.

11. The LCP of claim 1, wherein the controller is configured to:
    detect an S2 heart sound via the pressure sensor and/or the accelerometer;
    detect an A-wave via the pressure sensor;
    determine the ventricle pace time to achieve a smaller S2 to A-wave interval when the indication of metabolic demand exceeds a relaxation threshold; and
    determine the ventricle pace time to achieve a larger S2 to A-wave interval when the indication of metabolic demand does not exceed the relaxation threshold.

12. The LCP of claim 1, wherein controller is configured to:
- detect an S2 heart sound via the pressure sensor and/or the accelerometer;
- detect an S1 heart sound via the pressure sensor and/or the accelerometer;
- determine the ventricle pace time to achieve a smaller S2 to S1 interval when the indication of metabolic demand exceeds a relaxation threshold; and
- determine the ventricle pace time to achieve a larger S2 to S1 interval when the indication of metabolic demand does not exceed the relaxation threshold.

13. A leadless cardiac pacemaker (LCP) configured to sense cardiac activity and to pace a patient's heart, the LCP disposable within a ventricle of the patient's heart, the LCP comprising:
- a housing;
- a first electrode secured relative to the housing;
- a second electrode secured relative to the housing, the second electrode spaced from the first electrode;
- a controller disposed within the housing and operably coupled to the first electrode and the second electrode such that the controller is capable of receiving an electrical cardiac signal from the patient's heart via the first electrode and the second electrode;
- a pressure sensor disposed relative to the housing and operably coupled to the controller, the controller configured to receive a pressure sensor signal from the pressure sensor, wherein the pressure sensor signal is responsive to an atrial contraction of the patient's heart;
- an accelerometer disposed relative to the housing and operably coupled to the controller, the controller configured to receive an accelerometer signal from the accelerometer, wherein the accelerometer signal is responsive to an atrial contraction of the patient's heart;
- the controller configured to determine a ventricle pace time for delivering a ventricle pacing pulse to the ventricle of the patient's heart, the controller determining the ventricle pace time based at least in part on an indication of an atrial contraction event of the patient's heart and an indication of a current posture of the patient, wherein the indication of an atrial contraction event is based primarily or exclusively on the received accelerometer signal if the indication of the posture of the patient is reclined, and is based primarily or exclusively on the received pressure signal if the indication of the posture of the patient is upright; and
- the controller is configured to generate and deliver a ventricle pacing pulse at the ventricle pace time.

14. The LCP of claim 13, wherein the controller is configured to determine the indication of the posture of the patient based at least in part on the accelerometer signal.

15. The LCP of claim 13, wherein the controller is configured to:
- determine the ventricle pace time based at least in part on an LV pressure parameter indicated in the pressure sensor signal when the indication of the posture of the patient is upright; and
- determine the ventricle pace time based at least in part on a heart sound indicated in the pressure sensor signal and/or in the accelerometer signal when the indication of the posture of the patient is reclined.

16. The LCP of claim 13, wherein the controller is configured to:
- determine the ventricle pace time to achieve lower passive ventricular filling when the indication of the posture of the patient is upright; and
- determine the ventricle pace time to achieve higher passive ventricular filling when the indication of the posture of the patient is reclined.

* * * * *